United States Patent
Neves et al.

(10) Patent No.: US 11,168,367 B2
(45) Date of Patent: Nov. 9, 2021

(54) FLEXIBLE AND HIGH-THROUGHPUT SEQUENCING OF TARGETED GENOMIC REGIONS

(71) Applicant: RAPID GENOMICS LLC, Gainesville, FL (US)

(72) Inventors: Leandro Gomide Neves, Gainesville, FL (US); Adam Payton, Salt Lake City, UT (US)

(73) Assignee: RAPiD Genomics LLC, Gainesville, FL (US)

( * ) Notice: Subject to any disclaimer, the term of this patent is extended or adjusted under 35 U.S.C. 154(b) by 0 days.

(21) Appl. No.: 16/887,280

(22) Filed: May 29, 2020

(65) Prior Publication Data

US 2020/0377943 A1 Dec. 3, 2020

Related U.S. Application Data

(60) Provisional application No. 62/854,458, filed on May 30, 2019.

(51) Int. Cl.
- *C12Q 1/6876* (2018.01)
- *C12Q 1/6853* (2018.01)
- *C12Q 1/686* (2018.01)

(52) U.S. Cl.
CPC .......... *C12Q 1/6876* (2013.01); *C12Q 1/686* (2013.01); *C12Q 1/6853* (2013.01);
(Continued)

(58) Field of Classification Search
None
See application file for complete search history.

(56) References Cited

U.S. PATENT DOCUMENTS

| 4,656,127 A | 4/1987 | Mundy |
| 8,460,866 B2 | 6/2013 | Van Eijk et al. |

(Continued)

FOREIGN PATENT DOCUMENTS

| WO | WO 00/77260 | 12/2000 |
| WO | WO 2005/118847 | 12/2005 |

(Continued)

OTHER PUBLICATIONS

Krishnakumar's Supporting Information [online] available at: https://www.pnas.org/content/pnas/suppl/2008/07/02/0803240105.DCSupplemental/0803240105SI.pdf (Year: 2008).*

(Continued)

*Primary Examiner* — Samuel C Woolwine
(74) *Attorney, Agent, or Firm* — Saliwanchik, Lloyd & Eisenschenk

(57) ABSTRACT

The disclosure pertains to materials and methods for capturing a target genomic region, comprising hybridizing an extension probe and a ligation probe to target sequences that flank the target genomic region; elongating the 3' end of the extension probe until the 3' end of the elongated extension probe is adjacent to the 5' end of the ligation probe; and ligating the 3' end of the elongated extension probe with the 5' end of the ligation probe to produce a ligated probe. The ligated probe can be PCR amplified to produce copies of the target genomic region that can be detected or sequenced. Certain embodiments of the invention also provide methods of producing double stranded probes suitable for capturing and analyzing both strands of a target genomic region in a double stranded genomic DNA. The invention also provides kits for performing the methods disclosed herein.

8 Claims, 6 Drawing Sheets
(6 of 6 Drawing Sheet(s) Filed in Color)
Specification includes a Sequence Listing.

(52) U.S. Cl.
CPC .. *C12Q 2525/204* (2013.01); *C12Q 2561/113* (2013.01); *C12Q 2600/156* (2013.01); *C12Q 2600/16* (2013.01)

(56) References Cited

U.S. PATENT DOCUMENTS

| | | | |
|---|---|---|---|
| 8,795,968 | B2 | 8/2014 | Mindrinos et al. |
| 8,808,991 | B2 | 8/2014 | Hodgers |
| 2003/0024010 | A1* | 1/2003 | Cahoon .................. C12N 9/00 800/281 |
| 2008/0026393 | A1 | 1/2008 | Mindrinos et al. |
| 2009/0215633 | A1 | 8/2009 | Van Eijk et al. |
| 2011/0033920 | A1* | 2/2011 | Hartley ................. C12N 15/11 435/320.1 |
| 2014/0113839 | A1 | 4/2014 | Wu et al. |
| 2015/0133316 | A1 | 5/2015 | Kirst et al. |
| 2015/0141257 | A1 | 5/2015 | Albert et al. |
| 2018/0355406 | A1* | 12/2018 | Glover ................. C12Q 1/6806 |

FOREIGN PATENT DOCUMENTS

| | | |
|---|---|---|
| WO | WO 2009/079488 | 6/2009 |
| WO | WO 2012/021749 | 2/2012 |

OTHER PUBLICATIONS

Cantsilieris, S. et al. "Targeted Capture and High-Throughput Sequencing Using Molecular Inversion Probes (MIPs)" *Methods Mol. Biol.*, 2017 pp. 1-11, vol. 1492.

Jeuken, J. et al. "Multiplex Ligation-Dependent Probe Amplification; A Diagnostic Tool for Simultaneous Identification of Different Genetic Markers in Glial Tumors" *Journal of Molecular Diagnostics*, Sep. 2006, pp. 433-443, vol. 8, No. 4.

Campbell, N. R. et al. "Genotyping-in-Thousands by sequencing (GT-seq): A cost effective SNP genotyping method based on custom amplicon sequencing" *Molecular Ecology Resources*, 2015, pp. 855-867, vol. 15.

Gnirke, A. et al. "Solution Hybrid Selection with Ultra-long Oligonucleotides for Massively Parallel Targeted Sequencing" *Nat. Biotechnol.*, Feb. 2009, pp. 1-24, vol. 27, No. 2.

Shen, P. et al. "High-quality DNA sequence capture of 524 disease candidate genes" *PNAS*, Apr. 19, 2011, pp. 6549-6554, vol. 108, No. 16.

Krishnakumar, S. et al. "A comprehensive assay for targeted multiplex amplification for human DNA sequences" *PNAS*, Jul. 8, 2008, pp. 9296-9301, vol. 105, No. 27.

El-Sagheer, A. H. et al. "Biocompatible artificial DNA linker that is read through DNA polymerases and is functional in *Escherichia coli*" *PNAS*, Jul. 12, 2011, pp. 11338-11343, vol. 108, No. 28.

Shaw, J.-P. et al. "Modified deoxyoligonucleotides stable to exonuclease degradation in serum" *Nucleic Acids Research*, 1991, pp. 747-750, vol. 19, No. 4.

Simeonov, A. et al. "Single nucleotie polymorphism genotyping using short, fluorescently labeled locked nucleic acid (LNA) probes and fluorescence polarization detection" *Nucleic Acids Research*, 2002, pp. 1-5, vol. 30, No. 17, e91.

Shen, P. et al. "Multiplex target capture with double-stranded DNA probes" *Genome Medicine*, 2013 pp. 1-8, vol. 5, No. 50.

* cited by examiner

SEQUENCE LISTING

```
<160> NUMBER OF SEQ ID NOS: 4

<210> SEQ ID NO 1
<211> LENGTH: 11
<212> TYPE: DNA
<213> ORGANISM: Artificial Sequence
<220> FEATURE:
<223> OTHER INFORMATION: recognition site
<220> FEATURE:
<221> NAME/KEY: misc_feature
<222> LOCATION: (3)..(6)
<223> OTHER INFORMATION: n is a, c, g, or t
```

```
<400> SEQUENCE: 1
acnnnngtay c                                                    11

<210> SEQ ID NO 2
<211> LENGTH: 12
<212> TYPE: DNA
<213> ORGANISM: Artificial Sequence
<220> FEATURE:
<223> OTHER INFORMATION: recognition site
<220> FEATURE:
<221> NAME/KEY: misc_feature
<222> LOCATION: (4)..(9)
<223> OTHER INFORMATION: n is a, c, g, or t

<400> SEQUENCE: 2
cgannnnnnt gc                                                   12

<210> SEQ ID NO 3
<211> LENGTH: 11
<212> TYPE: DNA
<213> ORGANISM: Artificial Sequence
<220> FEATURE:
<223> OTHER INFORMATION: recognition site
<220> FEATURE:
<221> NAME/KEY: misc_feature
<222> LOCATION: (3)..(7)
<223> OTHER INFORMATION: n is a, c, g, or t

<400> SEQUENCE: 3
acnnnnnctc c                                                    11

<210> SEQ ID NO 4
<211> LENGTH: 12
<212> TYPE: DNA
<213> ORGANISM: Artificial Sequence
<220> FEATURE:
<223> OTHER INFORMATION: recognition site
<220> FEATURE:
<221> NAME/KEY: misc_feature
<222> LOCATION: (4)..(8)
<223> OTHER INFORMATION: n is a, c, g, or t

<400> SEQUENCE: 4
caannnnngt gg                                                   12
```

FLEXIBLE AND HIGH-THROUGHPUT SEQUENCING OF TARGETED GENOMIC REGIONS

CROSS-REFERENCE TO RELATED APPLICATION

This application claims the benefit of U.S. Provisional Application Ser. No. 62/854,458, filed May 30, 2019, the disclosure of which is hereby incorporated by reference in its entirety, including all figures, tables and amino acid or nucleic acid sequences.

The Sequence Listing for this application is labeled "Seq-List.txt" which was created on May 15, 2020 and is 2 KB. The entire content of the sequence listing is incorporated herein by reference in its entirety.

BACKGROUND OF THE INVENTION

Targeted sequencing is growing in importance as more robust and affordable sequencing technologies become available. The majority of the conventional methods for analyzing target regions of the genome involve target hybridization and capture (Gnirke et al., 2009), multiplex PCR (Campbell et al., 2015) or molecular inversion probes (Shen et al., 2011). These methods are either expensive, difficult to optimize, have high data variability, or lack flexibility to sequence targets of different length. Therefore, improved methods are desirable for analyzing, such as detecting and sequencing target genomic regions, particularly, detecting and sequencing target genomic regions that contain or are expected to contain genetic polymorphisms.

BRIEF SUMMARY OF THE INVENTION

Certain embodiments disclosed herein provide materials and methods for capturing target genomic regions and optionally, further analyzing the target genomic regions, such as by detection and/or sequencing. Preferably, the target genomic regions contain or are expected to contain genetic polymorphisms.

In certain embodiments, the methods disclosed herein for capturing a target genomic region from a target genetic material comprise hybridizing an extension probe and a ligation probe to a first target sequence and a second target sequence, wherein the first target sequence and the second target sequence flank the target genomic region; elongating the 3' end of the extension probe until the 3' end of the elongated extension probe is adjacent to the 5' end of the ligation probe; and ligating the 3' end of the elongated extension probe with the 5' end of the ligation probe to produce a ligated probe, the ligated probe comprising the target genomic region, thus capturing the target genomic region.

The ligated probe can be optionally purified from the reaction mixture and PCR amplified with an amplification primer pair to produce double stranded copies of the ligated probe that are suitable for further detection and/or sequencing. Sequencing can be performed using next generation sequencing techniques such as, nanopore sequencing, reversible dye-terminator sequencing, Single Molecule Real-Time (SMRT) sequencing or paired end sequencing.

Further embodiments of the invention provide methods of producing extension and ligation probes in a double stranded form. Using the probes in the double stranded form allows capturing both strands of a double stranded target genomic region.

In certain embodiments, a plurality of target genomic regions in a genetic material are captured using a plurality of pairs of probes, each pair of probes comprising an extension probe and a ligation probe, amplifying the extension probes hybridized to the corresponding target sequences and ligating the amplified extension probes with the corresponding ligation probes to capture the plurality of target genomic regions. The ligated probes can be optionally purified from the reaction mixture and PCR amplified with an amplification primer pair to produce double stranded copies of the target genomic regions that are suitable for further detection and sequencing. A plurality of ligated probes from a plurality of samples can be pooled to sequence in a multiplex sequencing reaction. The amplification primers can comprise unique identifier sequences to identify the source of the amplified target genomic regions. After the sequencing step, the sample specific unique identifiers are used to allocate a sequence to a sample and the sequence of the captured target genomic region is compared to known databases to allocate the sequence to a target genomic region in the sample. Sequencing can be performed using next generation sequencing techniques such as, nanopore sequencing, reversible dye-terminator sequencing, Single Molecule Real-Time (SMRT) sequencing, or paired end sequencing.

Further embodiments of the invention provide kits for carrying out the methods disclosed herein. The kits comprise one or more of: one or more pairs of extension probes and ligation probes, enzymes, such as DNA ligase, DNA polymerase, one or more amplification primer pairs, reagents for sequencing and instructions for conducting the assays.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

DETAILED DISCLOSURE OF THE INVENTION

Figure 1:
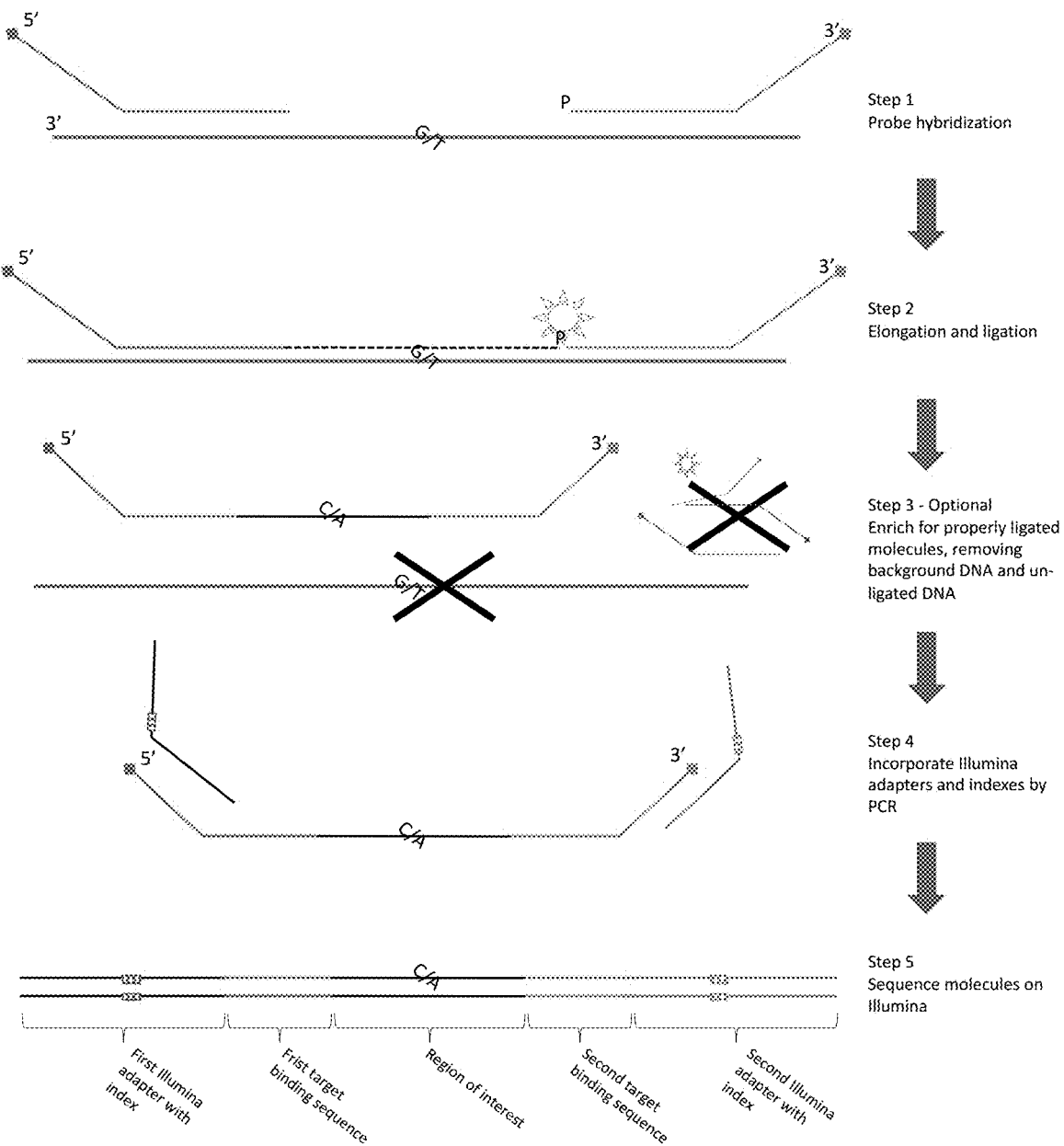
FIG. 1. Overview of one example of capturing and sequencing a target genomic region according to the methods disclosed herein.
Figure 2:
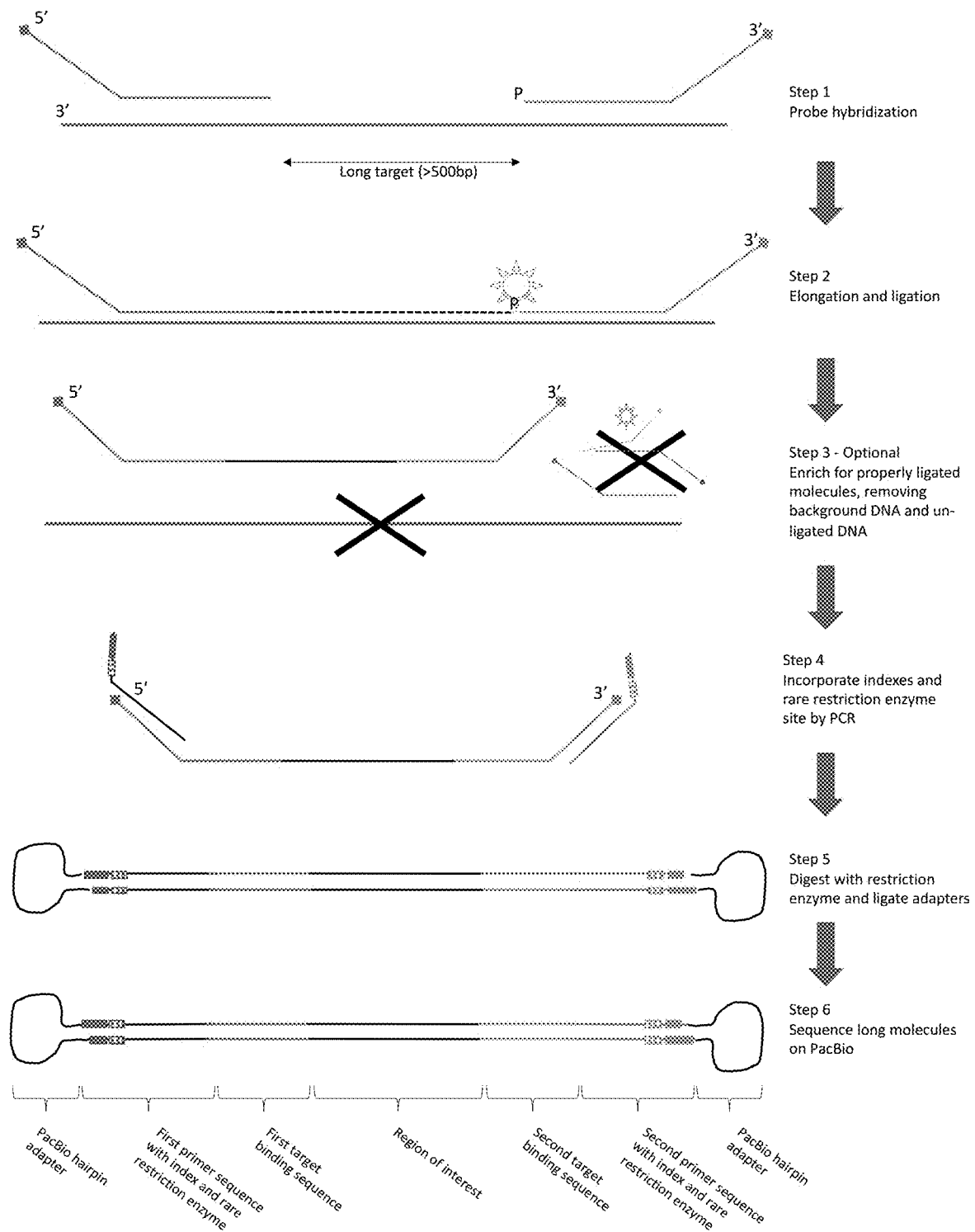
FIG. 2. Overview of one example of capturing and sequencing a long target genomic region according to the methods disclosed herein.

As used herein, the singular forms "a", "an" and "the" are intended to include the plural forms as well, unless the context clearly indicates otherwise. To the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrase "consisting essentially of" or "consists essentially of" indicates that the described embodiment encompasses embodiments containing the specified materials or steps and those that do not materially affect the basic and novel characteristic(s) of the described embodiment.

The term "about" means within an acceptable error range for the particular value as determined by one of ordinary skill in the art, which will depend in part on how the value is measured or determined, i.e., the limitations of the measurement system. In the context of the lengths of polynucleotides where the terms "about" are used, these polynucleotides contain the stated number of bases or base-pairs with a variation of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, such as for the size of the polynucleotides, the combinations and sub-combinations of the ranges (e.g., subranges within the disclosed range) and specific embodiments therein, are explicitly included.

The term "organism" as used herein includes viruses, bacteria, fungi, plants and animals. Additional examples of organisms are known to a person of ordinary skill in the art and such embodiments are within the purview of the materials and methods disclosed herein. The assays described herein can be useful in analyzing any genetic material obtained from any organism.

The term "genome", "genomic", "genetic material" or other grammatical variation thereof as used herein refers to genetic material from any organism. A genetic material can be viral genomic DNA or RNA, nuclear genetic material, such as genomic DNA, or genetic material present in cell organelles, such as mitochondrial DNA or chloroplast DNA. It can also represent the genetic material coming from a natural or artificial mixture or a mixture of genetic material from several organisms.

As used herein, "a target genomic region" is a region of interest in a genetic material of an organism.

The term "hybridizes with" when used with respect to two sequences indicates that the two sequences are sufficiently complementary to each other to allow nucleotide base pairing between the two sequences. Sequences that hybridize with teach other can be perfectly complementary but can also have mismatches to a certain extent. Therefore, the sequences at the 5' and 3' ends of the extension and ligation probes described herein may have a few mismatches with the corresponding target sequences at the 5' and 3' ends of the target genomic region as long as the extension and the ligation probes can hybridize with the target sequences to facilitate capturing of the target genomic region. Depending upon the stringency of hybridization, a mismatch of up to about 5% to 20% between the two complementary sequences would allow for hybridization between the two sequences. Typically, high stringency conditions have higher temperature and lower salt concentration and low stringency conditions have lower temperature and higher salt concentration. High stringency conditions for hybridization are preferred, and therefore, the sequences at the 3' and 5' ends of the extension and ligation probes are preferred to be perfectly complementary to the corresponding target sequences at the 3' and 5' ends of the target genomic region.

The term "identifier" as used herein refers to a known nucleotide sequence of between four to one hundred nucleotides, preferably, between ten to twenty nucleotides, and even more preferably, about eight or sixteen nucleotides. The appropriate length of identifier sequences depends on the sequencing technology being used. Once incorporated into the amplified target genomic regions, the identifier sequences can facilitate sequencing and identification of the target genomic regions, for example, by providing unique identification sites that allow allocating the correct sequences to the correct target genomic regions.

The term "paired-end sequencing" used herein refers to the sequencing technology where both ends of a double stranded polynucleotide are sequenced using specific primer binding sites present on each end of the double stranded polynucleotide. Paired-end sequencing generates high-quality sequencing data, which is aligned using a computer software program to generate the sequence of the polynucleotide flanked by the two primer binding sites. Sequencing from both ends of a double stranded molecule allows high quality data from both ends of the double stranded molecule because sequencing from only one end of the molecule may cause the sequencing quality to deteriorate as longer sequencing reads are performed.

In the paired-end sequencing, the double stranded amplified ligated probes produced at the end of the PCR amplification step of the methods disclosed herein are sequenced using specific primers that bind to the two ends of the double stranded ligated probes. A general description and the principle of paired-end sequencing is provided in Illumina Sequencing Technology, Illumina, Publication No. 770-2007-002, the contents of which are herein incorporated by reference in their entirety.

Non-limiting examples of the paired-end sequencing technology are provided by Illumina MiSeq™, Illumina MiSeqDx™ and Illumina MiSeqFGx™. Additional examples of the paired-end sequencing technology that can be used in the assays disclosed herein are known in the art and such embodiments are within the purview of the invention.

As used herein, the phrase "hairpin adapter" refers to a polynucleotide containing a double stranded stem and a single stranded hairpin loop. The single stranded hairpin loop region of a hairpin adapter can provide primer binding site for sequencing. Thus, once a hairpin adapter hybridizes with both sticky ends of a target genomic sequence, it produces a double-stranded DNA template containing the target genomic region in the double stranded region capped by hairpin loops at both ends. Such template can be used for sequencing the target genomic region via Single Molecule Real-Time (SMRT) sequencing (PacBio™). Description and the principle of SMRT sequencing is provided in Pacific Biosciences (2018), Publication No. BR108-100318, the contents of which are herein incorporated by reference in their entirety.

Nanopore technology may be used in the methods disclosed herein to sequence the target genomic regions. In certain such embodiments, the copies of target genomic regions are processed to sequence the target genomic regions as described, for example, in Nanopore Technology Brochure, Oxford Nanopore Technologies (2019), and Nanopore Product Brochure, Oxford Nanopore Technologies (2018). The contents of both these brochures are herein incorporated by reference in their entireties.

Throughout this disclosure, different sequences are described by specific nomenclature, for example, a primer binding sequence, primer sequence, identifier sequence, sequencing primer binding sequence and sequencing primer sequence. When such nomenclature is used, it is understood that the identified sequence is substantially identical or substantially reverse complementary to at least a part of the corresponding sequence. For example, "a primer sequence" describes a sequence that is substantially identical to at least a part of the primer sequence or substantially reverse complementary to at least a part of the primer sequence. This is because when a captured target genomic region is converted into a double stranded form comprising the primer binding sequence, the double stranded target genomic region can be sequenced using a primer having a sequence that substantially identical or substantially reverse complementary to at least a part of primer binding sequence. Thus, the nomenclature is used herein to simplify the description of different polynucleotides and parts of polynucleotides used in the methods disclosed here; however, a person of ordinary skill in the art would recognize that appropriate substantially identical or substantially reverse complementary sequences to at least a part of the corresponding sequences could be used to practice the methods disclosed herein.

Also, two sequences that correspond to each other, for example, a primer binding sequence and a primer sequence or a sequencing primer binding sequence and a sequencing primer sequence, have at least 90% sequence identity, preferably, at least 95% sequence identity, even more preferably, at least 97% sequence identify, and most preferably, at least 99% sequence identity, over at least 70%, preferably, at least 80%, even more preferably, at least 90%, and most preferably, at least 95% of the sequences. Alternatively, two sequences that correspond to each other are reverse complementary to each other and have at least 90% perfect matches, preferably, at least 95% perfect matches, even more preferably, at least 97% perfect matches, and most preferably, at least 99% perfect matches in the reverse complementary sequences, over at least 70%, preferably, at least 80%, even more preferably, at least 90%, and most preferably, at least 95% of the sequences. Thus, two sequences that correspond to each other can hybridize with each other or hybridize with a common reference sequence over at least 70%, preferably, at least 80%, even more preferably, at least 90%, and most preferably, at least 95% of the sequences. Preferably, two sequences that correspond to each other are 100% identical over the entire length of the two sequences or 100% reverse complementary over the entire length of the two sequences.

This disclosure provides materials and methods that solve the problems associated with conventional methods for analyzing target genomic regions. Particularly, this disclosure provides materials and methods for analyzing a target genomic region, particularly, a target genomic region having or suspected of having a genetic polymorphism.

The methods disclosed herein provide capturing a target genomic region from a target genetic material. The methods comprise the steps of:

a) hybridizing an extension probe and a ligation probe to a first target sequence and a second target sequence, wherein the first target sequence and the second target sequence flank the target genomic region, wherein:

i) the extension probe comprises toward the 3' end a first target binding sequence and toward the 5' end a first primer binding sequence, and ii) the ligation probe comprises toward the 5' end a second target binding sequence and toward the 3' end a second primer binding sequence;

b) amplifying the 3' end of the extension probe until the 3' end of the amplified extension probe is adjacent to the 5' end of the ligation probe;

c) ligating the 3' end of the amplified extension probe with the 5' end of the ligation probe to produce a ligated probe, the ligated probe comprising, from the 5' end to the 3' end, the first primer binding sequence, the first target binding sequence, the amplified target genomic region, the second target binding sequence, and the second primer binding sequence.

The extension probe comprises toward the 3' end a sequence that hybridizes with a first target sequence. Such sequence on the extension probe is referenced herein as the first target binding sequence. The extension probe comprises toward the 5' end a first primer binding sequence. The first target binding sequence and the first primer binding sequence may have an intervening sequence that can provide additional functionality, such as, an identifier sequence.

The ligation probe comprises toward the 5' end a sequence that hybridizes with a second target sequence. Such sequence on the ligation probe is referenced herein as the second target binding sequence. The ligation probe comprises toward the 3' end a second primer binding sequence. The second target binding sequence and the second primer binding sequence may have an intervening sequence that can provide additional functionality, such as, an identifier sequence. The 5' end of the ligation probe has a phosphate group, which facilitates ligation of the ligation probe with the 3' end of the amplified extension probe.

Thus, the methods disclosed herein comprise a step of hybridization of a pair of specifically designed oligonucleotide probes to certain target sequences in a target genetic material. The target sequences flank the target genomic region. FIG. 1 shows a target genomic region containing an SNP and probes that hybridize non-adjacently to that SNP. The first probe (shown on the left of FIG. 1) is referenced herein as "the extension probe" and the second probe (shown on the right of FIG. 1) is referenced herein as "the ligation probe". The sequence at the 3' end of the extension probe hybridizes to the corresponding target sequence on the genetic material and the sequence at the 5' end of the ligation probe hybridizes to the corresponding target sequence on the genetic material. Thus, the extension probe and the ligation probe bind to the corresponding target sequences and these target sequences flank the target genomic region.

Each of the extension probe and the ligation probe can contain a minimum of between about 20 and about 60 nucleotides. Particularly, the first target binding sequence portion of the extension probe can be at least between about 10 and about 30 nucleotides. The first primer binding sequence of the extension probe can also be at least between about 10 and about 30 nucleotides. Similarly, the second target sequence of the ligation probe can be at least between about 10 and about 30 nucleotides and the second primer binding sequence of the ligation probe can be at least between about 10 and about 30 nucleotides. The specificity of the probes towards the target binding sites can be controlled by the lengths of the first and the second target binding sequences. Particularly, longer lengths of the first and the second target binding sequences provide higher binding specificity and shorter lengths of the first and the second target binding sequences provide lower specificity. A person of ordinary skill in the art can determine appropriate sequences for the first and the second target binding sequences based on the sequence of the target genomic region and the available genomic sequence for a particular organism, for example, from a genome sequence database.

The length of the target genomic region and, hence, the distance between target sequences of the two probes depends on the purpose of the analysis, the characteristics of the target genomic region, and when performed, the sequencing methods used for the analysis. For example, if the purpose is to discover a polymorphism in the target genomic region, for example, SNP, indel, deletion, or insertion, target genomic regions of about 100 to about 300 base pairs (bp) are analyzed. Also, if Illumina™ 2×150 bp sequencing method is used, target genomic regions of about 300 bp are analyzed. If paired-end or nanopore based sequencing technique is used, target genomic regions of about 1,000 bp to about 20,000 bp can be analyzed. Alternatively, if the purpose is to genotype an SNP, the target genomic region can be very short, for example, between about 10 bp and about 100 bp. In the methods disclosed herein, the target genomic region comprises at least two to fifty nucleotides. Therefore, the two probes hybridize non-adjacently on the target genetic material.

At the end of the hybridization step, the extension probe is hybridized to the first target sequence via the first target binding sequence and the ligation probe is hybridized to the second target sequence via the second target binding sequence. The first and the second target binding sequences flank the target genomic region.

The next step of the methods disclosed herein comprises an elongation reaction to elongate the extension probe, i.e., to extend the extension probe towards the ligation probe. The elongation of the extension probe is designed to fill the gap between the first target sequence and the second target sequence, i.e., the elongation reaction adds to the extension probe a sequence of the target genomic region.

The elongation of the extension probe can be carried out using a DNA polymerase that lacks strand-displacement ability. A DNA polymerase lacking the strand-displacing ability dissociates when it completely fills the gap between the first and second target sequences and, thus, disassociates when it reaches the 5' end of the ligation probe.

In a subsequent step, the 5' end of the ligation probe is ligated to 3' end of the elongated extension probe, for example, in a ligase mediated reaction.

For the purposes of this disclosure and with respect to the binding sites of the two probes, the term "non-adjacent" or "non-adjacently" indicates that when the two probes are hybridized to their respective target sequences 3' end of the extension probe cannot form a phosphodiester bond with the 5' end of the ligation probe. Conversely, with respect to the binding sites of the two probes, the term "adjacently" indicates that when the two probes are hybridized to their respective target sequences 3' end of the extension probe can form a phosphodiester bond with the 5' end of the ligation probe.

Because the methods disclosed herein involve filling the gap between the two probes in an elongation step, the probes can be designed to bind to the target sequences anywhere around the target region as long as such target sequences flank the target genomic region. Thus, the amplification step provides flexibility for probe design and increases the chances of identifying the polymorphisms from the target genomic regions. Additionally, because of the step of filling the gap, the probes can be designed based on sequences that do not have or are not expected to have polymorphism, which avoids designing multiple probes for identifying one polymorphism, such as, a single nucleotide polymorphism (SNP). Moreover, the elongated region can capture multiple polymorphisms and analyzing one target genomic region can provide information about multiple polymorphisms that may exist in the region flanked by the target sequences of a pair of probes.

At the end of the extension reaction, the extension probe is elongated with additional sequence and the 3' end of the elongated extension probe is adjacent to the 5' end of the ligation probe. Therefore, at the end of the extension reaction, the elongated extension probe and the ligation probe are a substrate for a ligation reaction.

Accordingly, the next step of the methods disclosed herein comprises ligating the 3' end of the elongated extension probe with the 5' end of the ligation probe. A ligation reaction can comprise forming a phosphodiester bond between the 3'-OH group of the elongated extension probe and 5'-phosphate group of the ligation probe. Thus, the two probes are joined together. In certain embodiments, to provide the 5'-phosphate group for the ligation reaction, the ligation probe is designed to have the 5'-phosphate group.

Thus, in certain embodiments of the ligation step, a ligase is provided, which covalently connects the 3' end of the elongated extension probe with the 5' end of the ligation probe. In preferred embodiments, the ligase is a DNA ligase. DNA ligases are enzymes capable of catalyzing the formation of a phosphodiester bond between (the ends of) two polynucleotide strands bound at adjacent sites on a complementary strand. DNA ligases usually require ATP (EC 6.5.1.1) or NAD (EC 6.5.1.2) as a cofactor to seal nicks in double stranded DNA. DNA ligases that can be used in the ligation step include T4 DNA ligase, *E. coli* DNA ligase, *Thermus aquaticus* (Taq) ligase, *Thermus thermophilus* DNA ligase, or *Pyrococcus* DNA ligase. Additional ligases suitable for use in the methods disclosed herein are known in the art and such embodiments are within the purview of the invention.

Ligation of the elongated extension probe and the ligation probe can also be mediated by conjugations other than phosphodiester linkage between 3'-OH and 5'-phosphate groups of the extension and ligation probes. Certain such ligations are described by El-Sagheer et al. (2011), *PNAS;* 108 (28) 11338-11343. Additional embodiments of artificial ligations that could be used to connect the ligation and extension probes are known in the art and such embodiments are within the purview of the invention.

In certain embodiments of the methods disclosed herein, the ligation step can be followed by a step designed to remove from the reaction mixture unwanted material, such as unincorporated probes, non-ligated extension products, for example, extension probes that result from probes binding off-target, and the target genomic DNA. This step is optional; however, when performed, it considerably improves the specificity of the reaction.

In certain embodiments, the removal of unwanted material is performed using an exonuclease. If an exonuclease is used for such removal, one or both of the extension and ligation probes are modified to protect the ligated probe from the exonuclease mediated digestion.

The exonuclease can have 5'-3' exonuclease activity, 3'-5' exonuclease activity, or both 5'-3' and 3'-5' exonuclease activities towards single-stranded and double-stranded nucleic acids. Non limiting examples of exonucleases that can be used in the methods disclosed herein include Exonuclease I, Exonuclease III, Exonuclease V, Exonuclease IV, Exonuclease T, Lambda Exonucleases, T7 Exonuclease, strandase exonuclease, and 3'-5' Exophosphodiesterases. A suitable exonuclease and corresponding protection of the extension and/or ligation probes can be selected by a person of ordinary skill in the art.

For example, when a 3'-5' exonuclease is used, the ligation probe is modified toward the 3' end. Preferably, such modification is on the nucleotide at the 3' end; however, a modification can also be made to a nucleotide not at the 3' end but distal to the 3' so that a 3'-5' exonuclease may cleave some of the nucleotides from the 3' end but would be blocked at the modified nucleotide and, thus, cannot cleave the entire ligated probe.

Alternatively, when a 5'-3' exonuclease is used, the extension probe is modified toward the 5' end. Preferably, such modification is on the nucleotide at the 5' end; however, a modification can also be made to a nucleotide not at the 5' end but distal to the 5' so that a 5'-3' exonuclease may cleave some of the nucleotides from the 5' end but would be blocked at the modified nucleotide and, thus, cannot cleave the entire ligated probe.

In certain embodiments, an exonuclease having both the 5'-3' and 3'-5' exonuclease is used or a combination of a 5'-3' exonuclease and a 3'-5' exonuclease is used. In such embodiments, the extension probe is modified toward the 5' end and the ligation probe is modified toward the 3' end. Preferably, such modification of the extension probe is on the nucleotide at the 5' end; however, a modification can also be made to a nucleotide not at the 5' end but distal to the 5' so that a 5'-3' exonuclease may cleave some of the nucleotides from the 5' end but would be blocked at the modified nucleotide and, thus, cannot cleave the entire ligated probe. Similarly, such modification of the ligation probe is on the nucleotide at the 3' end; however, a modification can also be made to a nucleotide not at the 3' end but distal to the 3' so that a 3'-5' exonuclease may cleave some of the nucleotides from the 3' end but would be blocked at the modified nucleotide and, thus, cannot cleave the entire ligated probe.

A person of ordinary skill in the art can determine appropriate modifications toward the 3' and/or the 5' ends. Such modifications include introducing thiophosphate linkages between nucleotides, incorporating two or more phosphoramidite and phosphoromonothioate and/or phosphorodithioate linkages toward the 5' and/or 3' ends of the oligonucleotide, replacing one or more phosphodiester linkages between adjacent nucleotides by a formacetal/ketal type linkage, blocking the 3' terminal hydroxyl group by a phosphoryl or acetyl group, introducing 3' terminal phosphoroamidate modification, introducing peptide nucleic acids (PNAs) or locked nucleic acids (LNAs), introducing one or more thiophosphate groups, or introducing 2-O-methyl ribose sugar groups in the oligonucleotide backbone.

Non-limiting examples of modifications useful in the methods disclosed herein are disclosed in the U.S. Pat. No. 4,656,127; Shaw et al., 1991, Nucleic Acids Research, 19, 747-750; Raney et al. (1998) in Peptide Nucleic Acids (Nielsen, P. E., and Egholm, M., Eds.) Horizon Scientific Press, Wymondham, U.K.; Simeonov et al, Nucl. Acids Res. 2002, Vol. 30, e31; and Jacobsen et al. Int. Biot. Lab, February 2001, 18. Each of these references is incorporated by reference herein in its entirety.

In certain embodiments, the removal of unwanted genetic material and the isolation of the ligated probes can be performed using a binding agent that specifically binds to a moiety conjugated to one or both of the ligation probe and the extension probe and is thus present in the ligated probe. For example, 5' end of the extension probe can be conjugated to biotin and the ligated probe can be isolated using specific binding of the ligated probe to streptavidin. Similarly, 3' end of the ligation probe can be conjugated to biotin and the ligated probes can be isolated using specific binding of the ligated probe to streptavidin.

Additional moieties that can be conjugated to the 5' or the 3' ends or within the ligation probe and/or the extension probe and the corresponding binding agents that can be used for the isolation of the ligated probe are known in the art and such embodiments are within the purview of the invention.

In certain embodiments, the end of the ligation step and the optional removal of unwanted material produce a ligated probe comprising, from the 5' end to the 3' end, the first primer binding sequence, the first target binding sequence, the amplified target genomic region, the second target binding sequence, and the second primer binding sequence. The formation and optional purification of the ligated probe signifies the capture of the target genomic region.

The ligated probe can be processed to prepare the ligated probe for further analysis. Such processing is designed to serve three main purposes, the amplification of the ligated probe, for example, via PCR, to detectable levels; the incorporation of sample-specific identifiers (also referenced in the art as indexes, barcodes, zip codes, adapters, etc.), and the incorporation into the ligated probe certain sequences that facilitate sequencing of the ligated probe and, thus, the target genomic region.

Therefore, in some embodiments, the ligated probe, containing the target genomic region captured in the form of elongated extension probe, is amplified to produce copies of the ligated probe. Such amplification can comprise producing in a PCR, copies of the ligated probe in double stranded form using an amplification primer pair. The amplification primer pair can be designed so that the resulting double stranded ligated probe, in addition to the target genomic region and the first and second primer binding sequences, further comprises one or more of: a first sequencing primer binding sequence, a first identifier sequence, a second sequencing primer binding sequence and a second identifier sequence.

In certain embodiments the amplification primer pair comprises:

i) an extension probe amplification primer comprising from the 5' to the 3' end, one or more of: a first sequencing primer binding sequence, a first identifier sequence, and the first primer sequence, and ii) a ligation probe amplification primer comprises from the 5' to the 3' end, one or more of: a second sequencing primer binding sequence, a second identifier sequence, and the second primer sequence.

In preferred embodiments, the amplification primer pair comprises:

i) an extension probe amplification primer comprising from the 5' to the 3' end: a first sequencing primer binding sequence, a first identifier sequence, and the first primer sequence, and ii) a ligation probe amplification primer comprises from the 5' to the 3' end: a second sequencing primer binding sequence, a second identifier sequence, and the second primer sequence.

In this step, a PCR is used to amplify the ligated probe using an amplification primer pair comprising an extension probe amplification primer and a ligation probe amplification primer. The ligation probe amplification primer binds to the 3' end of the ligated probe, i.e., toward the ligation probe side of the ligated probe. The extension probe amplification primer binds to the complement of the 5' end of the ligated probe, i.e., toward the extension probe side of the ligated probe.

The extension probe amplification primer comprises from the 5' to the 3' end, a first sequencing primer binding sequence, optionally, a first identifier sequence, and the first primer sequence. The first primer sequence hybridizes with the complement of the first primer binding sequence present toward the 5' end of the ligated probe. The first primer binding sequence is introduced into the ligated probe as a part of the extension probe.

The ligation probe amplification primer comprises from the 5' to the 3' end, a second sequencing primer binding sequence, optionally, a second identifier sequence, and the second primer sequence. The second primer sequence hybridizes with the second primer binding sequence present toward the 3' end of the ligated probe. The second primer binding sequence is introduced into the ligated probe as a part of the ligation probe.

In certain embodiments, one or both primers of the amplification primer pair comprises additional sequences that can facilitate downstream sequencing of the double stranded target genomic regions produced at the end of the amplification step. The additional sequences that can facilitate sequencing can contain, for example, at least a portion of the sequences required for flow-cell binding and sequencing primer binding to initiate sequencing on Illumina™ platform, such as paired end or single read sequencing, at least a portion of the hair-pin adapter required for hairpin adapter based sequencing, such as PacBio sequencing, or at least a portion of the sequences required for properly guiding the molecules through a nanopore technology based sequencer. When the resulting molecule contains only a portion of the sequences required for sequencing, the remainder can be introduced by any other fashion know in the art, such as adapter ligation.

The mixture of the ligated probe and the amplification primer pair is subjected to PCR.

In addition to the ligated probe and the amplification primer pair, the PCR reaction mixture may contain a DNA polymerase and other reagents for PCR, such as deoxyribonucleotides (dNTPs), metal ions (for example, $Mg^{2+}$ and $Mn^{2+}$), and a buffer. Additional reagents which may be used in a PCR reaction are well-known to a person of ordinary skill in the art and such embodiments are within the purview of the invention.

Typically, a PCR comprises 25 to 40 cycles, each cycle comprising a step of denaturation, annealing, and elongation at different temperatures. A step of final extension can be performed at the end of the last cycle of the PCR. Designing various aspects of a PCR, including the number of cycles and durations and temperatures of various steps within the cycle is apparent to a person of ordinary skill in the art and such embodiments are within the purview of the invention.

When the ligation probe amplification primer hybridizes with the ligated probe, the structure provided in FIG. 1, step 4, is produced. Thus, during the initial cycles of the PCR, the complementary copies of the ligated probe are produced with all components of the amplification primers. In the second cycle of the PCR, the extension probe amplification primer binds to the complementary copies of the ligated probes.

At the end of the PCR, multiple copies of the ligated probe in double stranded form containing the target genomic region are produced that are suitable for further analysis, such as detection or sequencing. An example of such double stranded DNA is provided in FIG. 1, step 5. This double stranded DNA comprises from one end to the other, the sequences corresponding to one or more of: first sequencing primer binding sequence, first identifier sequence, first primer sequence, first target sequence, a target genomic region, second target sequence, second primer sequence, second identifier, second sequencing primer binding sequence, and any additional sequences that can facilitate sequencing of the double stranded DNA containing the target genomic region.

The amplified target genomic region can be detected using techniques known in the art, for example, using a labeled probe complementary to a sequence within the target genomic region. For example, the amplified target genomic region can be detected based on the turbidity of the reaction, fluorescence detection or labeled molecular beacons.

The term "label" refers to a molecule detectable by spectroscopic, photochemical, biochemical, immunochemical, chemical, or other physical means. For example, useful labels include fluorescent dyes (fluorophores), fluorescent quenchers, luminescent agents, electron-dense reagents, biotin, digoxigenin, $^{32}P$ and other isotopes or other molecules that can be made detectable, e.g., by incorporating into an oligonucleotide. The term includes combinations of labeling agents, e.g., a combination of fluorophores each providing a unique detectable signature, e.g., at a particular wavelength or combination of wavelengths.

Exemplary fluorophores include, but are not limited to, Alexa dyes (e.g., Alexa 350, Alexa 430, Alexa 488, etc.), AMCA, BODIPY 630/650, BODIPY 650/665, BODIPY-FL, BODIPY-R6G, BODIPY-TMR, BODIPY-TRX, Cascade Blue, Cy2, Cy3, Cy5, Cy5.5, Cy7, Cy7.5, Dylight dyes (Dylight405, Dylight488, Dylight549, Dylight550, Dylight 649, Dylight680, Dylight750, Dylight800), 6-FAM, fluorescein, FITC, HEX, 6-JOE, Oregon Green 488, Oregon Green 500, Oregon Green 514, Pacific Blue, REG, Rhodamine Green, Rhodamine Red, ROX, R-Phycoerythrin (R-PE), Starbright Blue Dyes (e.g., Starbright Blue 520, Starbright Blue 700), TAMRA, TET, Tetramethylrhodamine, Texas Red, and TRITC.

The amplified target genomic region can also be sequenced using techniques known in the art, for example, nanopore sequencing (Oxford Nanopore Technologies™), reversible dye-terminator sequencing (Illumina™) and Single Molecule Real-Time (SMRT) sequencing (PacBio™). Various sequencing instruments can be used for sequencing, such as using portable Nanopore Minion™ or benchtop machines, Nanopore Promethion™, PacBio Sequel™ or Illumina HiSeq™. The sequencing step can also be used for multiplex detection of several targets and/or polymorphism detection. Preferably, the sequencing of the amplified target genomic regions is performed on a high-throughput sequencer, such as an Illumina, PacBio or Nanopore device.

A person of ordinary skill in the art can recognize that, depending upon specific aspects of an assay, such as the technology used for sequencing the target genomic region or the length of the target genomic region, one may not need to introduce all of the sequences described above during the amplification step. For example, the amplification primer pair can be designed where one or both of the identifier sequences are absent. An identifier sequence may not be necessary if only one target genomic region is studied. Also, both identifier sequences may not be necessary if the target genomic region is short, for example, less than about 500 bp.

Moreover, the amplification primer pair can be designed where one or both of the sequencing primer binding sequences are absent. For example, only one of the sequencing primer binding sequences may be sufficient for sequencing purposes if the target genomic region is short, for example, less than about 500 bp, or a single sequencing primer is required for sequencing (e.g. PacBio). In some cases, the ligation and extension probes can already contain at least a portion of the sequences required for sequencing, such as the sequencing primer binding sequence. Any additional sequences that can facilitate sequencing of the double stranded DNA containing the target genomic region can also be introduced via one or both primers of the amplification primer pair. Also, both the sequencing primer binding sequences may be absent and instead sequences can be introduced that facilitate further processing and subsequent sequencing of the double stranded amplified ligation probe. Such sequences include restriction enzyme sites, particularly, rare cutter restriction enzyme sites.

Non-limiting examples of rare-cutter restriction endonucleases are described in PCT Publication WO 2009/079488, which is herein incorporated by reference in its entirety, particularly, Table 1.

As used herein, "a rare-cutter restriction endonuclease" is an endonuclease whose restriction site occurs rarely in a genetic material. For example, for human genome, a rare-cutter restriction endonuclease is an endonuclease whose restriction site occurs on average every 50-100 kb, preferably, every 100-200 kb, or more preferably, every 200-400 kb, or even more preferably, every 400-600 Kb. Examples of rare-cutter restriction endonucleases for human genome and their restriction sites are given in Table 1 below:

TABLE 1

Examples of human rare-cutter endonucleases and their restriction sites.

| Restriction Enzyme | Recognition site | Frequency in Human genome (kb) |
|---|---|---|
| Not I | GCGGCCGC | 1000 |
| Xma III | CGGCCG | 100 |
| Sst II | CCGCGG | 100 |
| Sal I | GTCGAC | 100 |
| Nru I | TCGCGA | 300 |
| Nhe I | GCTAGC | 100 |

Additional rare-cutter endonucleases are described in, e.g., Restriction Endonucleases ((Nucleic Acids and Molecular Biology) by Pingoud (Editor), Springer; 1 ed. (2004)). Many rare-cutter endonucleases are also commercially available, such as homing class of endonucleases, e.g., from New England BioLabs (Beverly, Mass.). Even further examples of rare-cutter endonucleases are known in the art and such embodiments are within the purview of the invention.

The rare cutter restriction enzyme sites could be treated with the corresponding restriction enzymes and to produce double stranded amplified ligated probes having sticky ends. The sticky ends of the cleaved copies of the amplified target genomic regions can be used to conjugate the target genomic regions with hairpin adapters. For example, a hairpin adapter comprising overhangs complementary to the restriction sites introduced into the amplified target genomic regions via the amplification primer pairs can be mixed with the copies amplified target genomic regions treated with the restriction enzyme to produce a double stranded target genomic regions comprising the target genomic region flanked by, among other sequences, the hairpin adapters.

Additional restriction endonucleases sites corresponding to Type IIS restriction enzymes can be used to produce double stranded amplified ligated probes, including for use in tail-swapping. In preferred embodiments, BsaI and MlyI restriction endonuclease sites are used. MlyI provides a blunt end, while BsaI provides an overhang. Examples of Type IIS restriction endonucleases, their recognition sites, and the quantity of nucleotide overhang (if any) after a digestion using the respective enzyme are provided in Table 2 below:

TABLE 2

Examples of Type IIS endonucleases, their restriction sites, and the quantity of nucleotide overhang after a digestion using the respective enzyme.

| Restriction Enyme | Recognition site | Overhang |
|---|---|---|
| AcuI | CTGAAG(16/14) | 2 |
| AlwI | GGATC(4/5) | 1 |
| BaeI | (10/15)ACNNNNGTAYC(12/7) (SEQ ID NO: 1) | 5 & 5 |
| BbsI * | GAAGAC(2/6) | 4 |
| BbsI-HF * | GAAGAC(2/6) | 4 |
| BbvI | GCAGC(8/12) | 4 |
| BccI | CCATC(4/5) | 1 |
| BceAI | ACGGC(12/14) | 2 |
| BcgI | (10/12)CGANNNNNNTGC(12/10) (SEQ ID NO: 2) | 2 & 2 |
| BciVI | GTATCC(6/5) | 1 |
| BcoDI | GTCTC(1/5) | 4 |
| BfuAI | ACCTGC(4/8) | 4 |
| BmrI | ACTGGG(5/4) | 1 |
| BpmI | CTGGAG(16/14) | 2 |
| BpuEI | CTTGAG(16/14) | 2 |
| BsaI | GGTCTC(1/5) | 4 |
| BsaXI | (9/12)ACNNNNNCTCC(10/7) (SEQ ID NO: 3) | 3 & 3 |
| BseRI | GAGGAG(10/8) | 2 |
| BsgI | GTGCAG(16/14) | 2 |
| BsmAI | GTCTC(1/5) | 4 |
| BsmBI | CGTCTC(1/5) | 4 |
| BsmFI | GGGAC(10/14) | 4 |
| BsmI | GAATGC(1/-1) | 2 |
| BspCNI | CTCAG(9/7) | 2 |
| BspMI | ACCTGC(4/8) | 4 |
| BspQI | GCTCTTC(1/4) | 3 |

TABLE 2-continued

Examples of Type IIS endonucleases, their restriction sites, and the quantity of nucleotide overhang after a digestion using the respective enzyme.

| Restriction Enyme | Recognition site | Overhang |
|---|---|---|
| BsrDI | GCAATG(2/0) | 2 |
| BsrI | ACTGG(1/-1) | 2 |
| BtgZI | GCGATG(10/14) | 4 |
| BtsCI | GGATG(2/0) | 2 |
| BtsI-v2 | GCAGTG(2/0) | 2 |
| BtsIMutI | CAGTG(2/0) | 2 |
| CspCI | (11/13)CAANNNNNGTGG(12/10) (SEQ ID NO: 4) | 2 & 2 |
| EarI | CTCTTC(1/4) | 3 |
| EciI | GGCGGA(11/9) | 2 |
| Esp3I | CGTCTC(1/5) | 4 |
| FauI | CCCGC(4/6) | 2 |
| FokI | GGATG(9/13) | 4 |
| HgaI | GACGC(5/10) | 5 |
| HphI | GGTGA(8/7) | 1 |
| HpyAV | CCTTC(6/5) | 1 |
| MboII | GAAGA(8/7) | 1 |
| MlyI | GAGTC(5/5) | 0 |
| MmeI | TCCRAC(20/18) | 2 |
| MnlI | CCTC(7/6) | 1 |
| NmeAIII | GCCGAG(21/19) | 2 |
| PleI | GAGTC(4/5) | 1 |
| SapI | GCTCTTC(1/4) | 3 |
| SfaNI | GCATC(5/9) | 4 |

In certain embodiments, multiple target genomic regions are captured and optionally, further analyzed, such as detected or sequenced. For a plurality of target genomic regions, a plurality of pairs of extension and ligation probes is used. Each pair of extension and ligation probes contains unique first and second target binding sequences, depending on the sequence flanking the target genomic region. However, each of the plurality of pairs of extension and ligation probes can have the same first primer binding sequences and the same second primer binding sequences.

Accordingly, certain embodiments of the materials and methods disclosed herein provide for capturing a plurality of target genomic regions from a genetic material. The methods comprise the steps of:

a) hybridizing a plurality of pairs of probes to a plurality of pairs of target sequences, wherein each pair of the target sequences flanks one target genomic region from the plurality of target genomic regions, and wherein each pair of probes comprises an extension probe and a ligation probe and for each pair of probes:

i) the extension probe comprises toward the 3' end a first target binding sequence and toward the 5' end a first primer binding sequence, and ii) the ligation probe comprises toward the 5' end a second target binding sequence and toward the 3' end a second primer binding sequence, wherein the first target binding sequence and the second target binding sequence bind respectively to a first target sequence and a second target sequence that flank a target genomic region;

b) elongating the 3' ends of the extension probes until the 3' ends of the amplified extension probes are adjacent to the 5' ends of the corresponding ligation probes;

c) ligating the 3' ends of the amplified extension probes with the 5' end of the corresponding ligation probes to produce a plurality of ligated probes, each ligated probe comprising, from the 5' end to the 3' end, the first primer binding sequence, a first target binding sequence, an amplified target genomic region, a second target binding sequence, and the second primer binding sequence.

In certain embodiments, the components other than the ligated probes comprising one or more of unincorporated probes, non-ligated extension products, and the target genetic material can be removed.

The aspects described above of capturing a target genomic region, for example, designing the extension and ligation probes, the length of the target genomic regions, the first and second primer binding sequences are also applicable to the instant methods of capturing a plurality of target genomic regions.

In certain embodiments, the methods disclosed herein comprise amplifying the plurality of ligated probes in a PCR using an amplification primer pair to produce a plurality of double stranded ligated probes further comprising one or more of: a first sequencing primer binding sequence, a first identifier sequence, a second sequencing primer binding sequence and a second identifier sequence, wherein the amplification primer pair comprises:

i) an extension probe amplification primer comprising from the 5' to the 3' end, one or more of: a first sequencing primer binding sequence, a first identifier sequence, and the first primer sequence, and ii) a ligation probe amplification primer comprises from the 5' to the 3' end, one or more of: a second sequencing primer binding sequence, a second identifier sequence, and the second primer sequence.

Preferably, the amplification primer pair comprises:

i) an extension probe amplification primer comprising from the 5' to the 3' end: a first sequencing primer binding sequence, a first identifier sequence, and the first primer sequence, and ii) a ligation probe amplification primer comprising from the 5' to the 3' end: a second sequencing primer binding sequence, a second identifier sequence, and the second primer sequence.

In certain embodiments, one or both primers of the amplification primer pair comprises additional sequences that can facilitate downstream sequencing of the double stranded target genomic regions produced at the end of the amplification step. The additional sequences that can facilitate sequencing can contain, for example, at least a portion of the sequences required for flow-cell binding and sequencing primer binding to initiate sequencing on Illumina™ platform, such as paired end or single read sequencing, at least a portion of the hair-pin adapter required for hairpin adapter based sequencing, such as PacBio sequencing, or at least a portion of the sequences required for properly guiding the molecules through a nanopore technology based sequencer. When the resulting molecule contains only a portion of the sequences required for sequencing, the remainder can be introduced by any other fashion know in the art, such as adapter ligation.

To capture a plurality of target genomic regions from a genetic material, pairs of probes are designed to contain the same first and second primer binding sequences. Therefore, only one amplification primer pair can be used to amplify the plurality of captured target genomic regions from one sample. Also, the same first and second sequencing primer can be used in the subsequent sequencing reaction, if performed, to sequence the plurality of captured target genomic regions. Accordingly, one primer from the amplification primer pair contains one or more of: the first sequencing primer binding sequence, the first identifier sequence and the first primer sequence, whereas the other primer from the amplification primer pair contains one or more of: the second sequencing primer binding sequence, the second identifier sequence and the second primer sequence. The first and the second identifier sequences can be identical to each other and the first and the second primer sequences can be identical to each other.

Thus, at the end of the amplification step of a method for capturing a plurality of target genomic regions, copies of a plurality of amplified genomic regions are produced, each copy comprising: the first sequencing primer binding sequence, the first identifier sequence, the first primer sequence, one of the plurality of target genomic regions, the second primer sequence, the second identifier sequence, and the second sequencing primer sequence.

In certain embodiments, the plurality of target genomic regions are further analyzed, for example, detected or sequenced. The amplified target genomic regions can be detected using techniques known in the art, for example, using a plurality of labeled probes complementary to sequences within the target genomic regions. For example, the amplified target genomic regions can be detected based on the turbidity of the reaction, fluorescence detection or labeled molecular beacons. The aspects described above of detecting a target genomic region are also applicable to detecting a plurality of genomic regions.

The plurality of amplified target genomic regions can also be sequenced using techniques known in the art. The aspects described above of detecting a target genomic region are also applicable to detecting a plurality of genomic regions.

Particularly, in certain embodiments, a plurality of target genomic regions from a plurality of samples are pooled and sequenced. In such embodiments, a plurality of sequence reads is obtained corresponding to a plurality of target genomic regions from the plurality of samples. For a particular read, the unique first and/or second identifier sequences are used to allocate the read to the corresponding sample and the sequence of the captured target genomic region in the read is compared to known databases to allocate the sequence to a target genomic region in the sample. Thus, while only one or two sequencing primers could be used to sequence many target genomic regions in one reaction mixture, each of the sequencing reads can be systematically and accurately attributed to the appropriate source sample and appropriate target genomic region.

In certain embodiments, a plurality of target genomic regions in a sample from a plurality of samples is amplified using an amplification primer pair that contains a unique combination of two sequence identifiers. Therefore, no two samples from the plurality of samples have the same combination of the first and the second identifiers. For example, twelve unique first identifiers and eight unique second identifiers can be used to produce ninety-six unique combinations of the first and the second identifiers. Thus, using different combinations of only twenty identifiers, ninety-six samples could be uniquely identified.

In such embodiments, for a particular read, the unique first identifier sequence and the second identifier sequence is used to allocate the read to the corresponding sample and the sequence of the captured target genomic region in the read is compared to known databases to allocate the sequence to a target genomic region in the sample. Thus, while only one or two sequencing primers could be used to sequence many target genomic regions in one reaction mixture, each of the sequencing reads can be systematically and accurately attributed to the appropriate source sample and appropriate target genomic region.

Similar to detecting or sequencing a single target genomic region, a person of ordinary skill in the art can recognize that, some of the sequences in the amplification primer pair may not be present depending upon how the amplification primer pair is designed. For example, only one identifier sequence may be present or only one sequencing primer binding sequence may be present, particularly, when the analyzed target genomic regions are short, such as less than about 500 bp, or a single sequencing primer is required for sequencing (e.g. PacBio). In some cases, the ligation and extension probes can already contain at least a portion of the sequences required for sequencing, such as the sequencing primer binding sequence. Any additional sequences that can facilitate sequencing of the double stranded DNA containing the target genomic region can also be introduced via one or both primers of the amplification primer pair. Also, both the sequencing primer binding sequences may be absent and instead sequences can be introduced that facilitate further processing and subsequent sequencing of the double stranded amplified target genomic regions. Such sequences include restriction enzyme sites, particularly, rare cutter restriction enzyme sites. The rare-cutter restriction enzymes discussed above can also be used in these embodiments of the invention.

Kits for carrying out the methods disclosed herein are also envisioned. Certain such kits can contain specific extension probes and ligation probes designed to capture one or more target genomic regions, extension probe amplification primers, ligation probe amplification primers to amplify one or more captured target genomic regions, DNA ligase, polymerase and other reagents for PCR, sequencing reagents, computer software program designed to process the sequencing data obtained from the assay and optionally, materials that provide instructions to perform the assay.

In certain embodiments, the kits can be customized for one or more specific target genomic regions. For example, a user may provide the sequences of one or more target genomic regions and a kit can be produced to carry out the assay disclosed herein for analyzing the one or more target sequences.

The synthesis of the extension and ligation probes used in the methods disclosed herein is typically expensive, particularly, if the probes contain modifications, such as 5' phosphate and/or modified oligonucleotides. The conventional methods for synthesizing such probes, for example, by commercial vendors, involve phosphoroamidite approach. This approach comprises synthesizing and purifying one oligonucleotide at a time, ultimately yielding a collection of single-stranded oligonucleotides.

The methods disclosed herein to analyze a target genomic region require two oligonucleotides for each target region because the ligation and extension probes bind to sequences that flank the target genomic region. The conventional technologies use allele-specific oligonucleotides and, therefore, need three oligonucleotides per bi-allelic target genomic region. The methods disclosed herein provide an improvement over the conventional methods because these methods require only two oligonucleotides per target genomic region.

Even with the reduced cost of synthesizing two oligonucleotides per target genomic region compared to three oligonucleotides per target genomic region, further reduction is desirable in the cost for synthesizing a pair of ligation and extension probes. Considering that the claimed methods can be used to simultaneously analyze multiple target genomic regions, the reduction in the cost of synthesizing a pair of ligation and extension probes is reflected exponentially in the total cost savings for an assay designed to analyze thousands of target genomic regions.

To that end, certain embodiments of the invention provide methods for producing the ligation and/or extension probes in double stranded form for use in the methods disclosed herein. These methods are scalable and reduce the cost of synthesizing the oligonucleotides typically by at least 10 times and potentially even 100 to 1,000 times.

Certain embodiments of invention provide a method of producing double stranded probes from a single stranded oligonucleotide. The approach is designed for producing the double stranded probe that target both strands of the chromosome and constitute extension and ligation probes relative to each strand, respectively. Such single stranded oligonucleotide is referenced herein as "a single stranded pre-probe". To allow for the addition of modifications and inclusion of at least a portion of the sequences required for sequencing, such as the sequencing primer binding sequence, two or more groups of probes can be produced. As an example for sequencing on Illumina platforms, two groups of probes are constructed, herein defined as upstream and downstream probes, which contain sequences corresponding to at least a portion of the i5 and i7 Illumina adapter sequences, respectively. In certain embodiments, the upstream double-stranded probe hybridizes the left side of the target region, whereas the downstream double-stranded probe targets the right side of the target region. The method of producing a double stranded ligation and extension upstream probe comprises the steps of:

a) providing a single stranded or double stranded pre-probe comprising from the 5' end towards the 3' end: a first tail, a first restriction site for a first restriction enzyme, a target binding sequence, a second restriction site for a second restriction enzyme, and a second tail, wherein the double stranded pre-probe is optionally produced in a PCR using appropriate primers to copy the single stranded pre-probe, b) optionally, performing a tail-swap reaction to substitute a temporary first or second tail for a permanent tail that is genetically modified to comprise at least a portion of a new desired sequence comprising:
  i) digesting the double stranded pre-upstream probe with the first restriction enzyme to remove the first pre-upstream tail, or a portion of it, to produce an overhang, and
  ii) ligating to the double stranded pre-upstream probe digested with the first restriction enzyme to the permanent tail, the permanent tail molecule that contains genetic modifications and at least a portion of the upstream permanent tail comprising an overhang that is complementary to the overhang of the digested double stranded pre-upstream probe, c) optionally, purifying the double stranded pre-upstream probe ligated to the permanent tail, d) producing a double stranded upstream probe by digesting the double stranded pre-upstream probe containing the first tail or the permanent tail swapped in place of the first tail with the second restriction enzyme to remove the second tail and produce a sticky end or, preferably, a blunt end within the first target binding sequence, and e) optionally, purifying the double stranded upstream probe. In some embodiments, the double stranded probes can be converted into single stranded probes by methods known in the art, for example denaturation of the double stranded probes or by selectively degrading one of the strands.

In preferred embodiments, the first restriction enzyme is a type IIS that digests a double stranded DNA to produce a sticky end away from its recognition site and the second restriction enzyme is another type IIS that digests a double stranded DNA away from its recognition site and produces a blunt end cut in the DNA. In even preferred embodiments, the first restriction enzyme is BsaI and the second restriction enzyme is MlyI. In certain embodiments, the overhang can be at least 1, 2, 3, 4, 5 or more nucleotides. In preferred embodiments, the overhang is 1-5 nucleotides, more preferably 1-3 nucleotides, and most preferably 1-2 nucleotides.

In certain embodiments, a barcode is placed between the first restriction site and the target binding sequence and/or the target binding sequence and the second restriction site.

In certain embodiments, the probe construction can start directly from double stranded pre-upstream probes, therefore skipping the first PCR step to convert the single stranded to double stranded molecules or simply performing the PCR to amplify the amount of pre-upstream probes.

The sequence of the steps of digesting with the first restriction enzyme and the step of digesting with the second restriction enzyme can be interchanged or occur simultaneously. Particularly, digestion with the second restriction enzyme producing a preferred blunt end can be performed first followed by the digestion with the first restriction enzyme producing overhangs and ligation with the first swapped adapter. Regardless of the sequence of digestions, same double stranded upstream probe would be produced at the end of both digestions and ligation.

Figure 3:
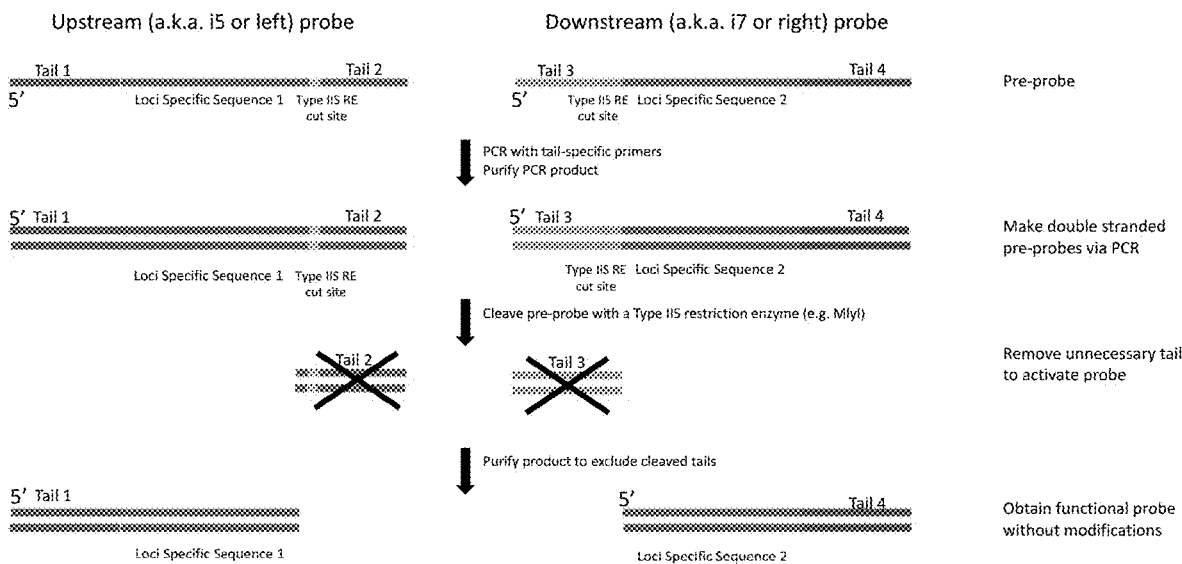
FIG. 3. Overview of one example of preparing probes in a double stranded form without a tail-swap for modifications.

As shown in FIG. 3, probes can be constructed without the tail swap step. Without a tail-swapping step, a restriction enzyme digest is performed to remove the unnecessary tail and activate the probes for hybridization. A single digestion reaction can be performed with at least 1, 2, 3, 4, or more restriction enzymes. Alternatively, digestion reactions can be performed in series, in which one restriction enzyme is removed or inactivated before the following restriction enzyme is added. The DNA resulting from the digestion reaction can have a blunt end. Any single-stranded overhang created by the reaction can be removed or the recessed strand can be filled-in using protocols well-known to those skilled in the art, such as the use of the Klenow fragment of DNA Polymerase I, to form a blunt end.

Figure 4:
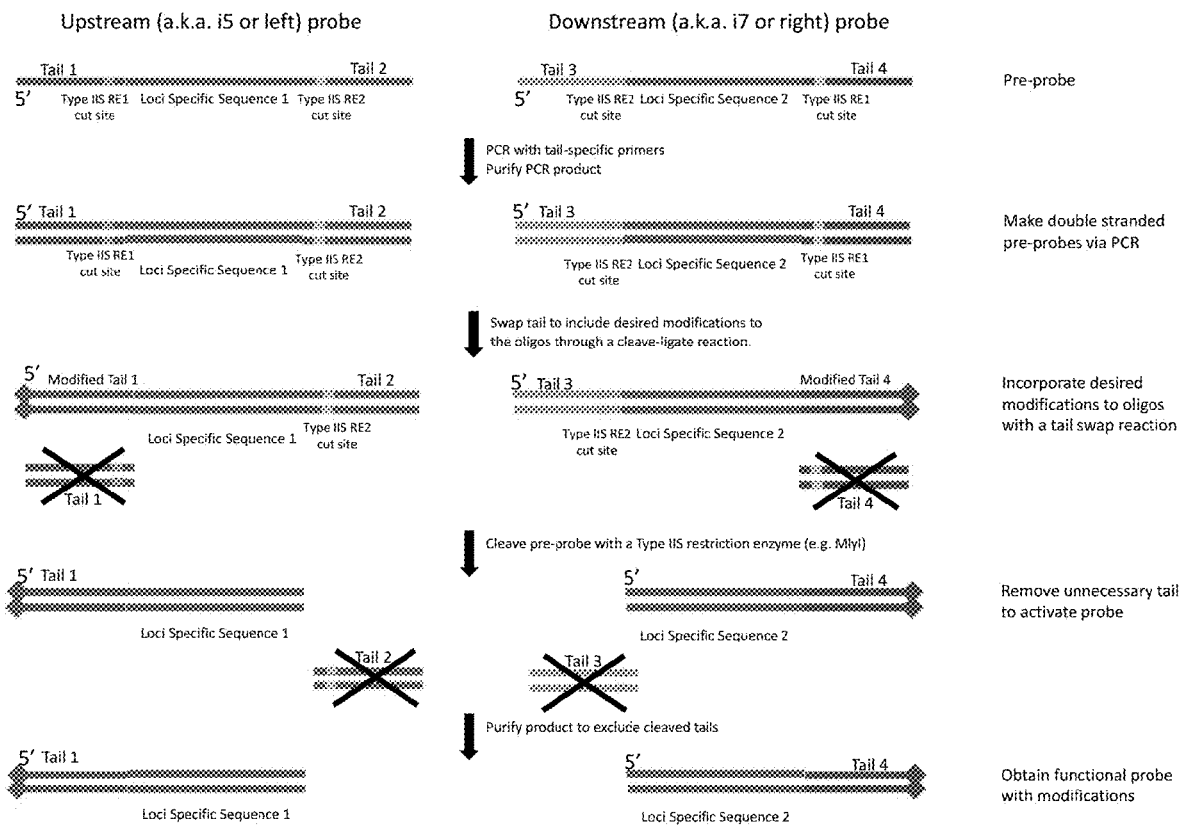
FIG. 4. Overview of one example of preparing probes in a double stranded form with a tail-swap to incorporate desirable modifications.

As shown in FIG. 4, the upstream probe is produced in a double stranded format. The upper strand having modifications on the 5' end corresponds to the extension probe discussed earlier in this disclosure. The other strand having the modifications on the 3' end corresponds to the ligation probe discussed earlier in this disclosure. Thus, in the double stranded upstream probes produced according to the methods disclosed herein, one strand is an extension probe suitable for analyzing one of the strands of the target genomic region and the other strand is a ligation probe suitable for analyzing the other strand of the target genomic region.

Further embodiments of invention provide a method of producing the double stranded downstream probe from a single stranded oligonucleotide designed that will target the right side of the target region. Such single stranded oligonucleotide is referenced herein as "a single stranded pre-downstream probe". The method of producing a double stranded downstream probe comprises the steps of:

a) providing a single stranded or double stranded pre-probe comprising from the 5' end towards the 3' end: a first tail, a first restriction site for a first restriction enzyme, a target binding sequence, a second restriction site for a second restriction enzyme, and a second tail, wherein the double stranded pre-probe is optionally produced in a PCR using appropriate primers to copy the single stranded pre-probe, b) optionally, performing a tail-swap reaction to substitute a temporary first or second tail for a permanent tail that is genetically modified to comprise at least a portion of a new desired sequence comprising:
  i) digesting the double stranded pre-downstream probe with the second restriction enzyme to remove the second pre-downstream tail, or a portion of it, to produce an overhang, and
  ii) ligating to the double stranded pre-downstream probe digested with the second restriction enzyme to the permanent tail, the permanent tail molecule that contains genetic modifications and at least a portion of the downstream permanent tail comprising an overhang that is complementary to the overhang of the digested double stranded pre-downstream probe, c) optionally, purifying the double stranded pre-downstream probe ligated to the permanent tail, d) producing a double stranded downstream probe by digesting the double stranded pre-downstream probe with the second tail or permanent tail swapped in place of the second tail with the first restriction enzyme to remove the first downstream tail and produce a sticky end or, preferably, a blunt end within the second target binding sequence, and e) optionally, purifying the double stranded downstream probe. In some embodiments, the double stranded probes can be converted into single stranded probes by methods known in the art, for example denaturation of the double stranded probes or by selectively degrading one of the strands.

In preferred embodiments, the second restriction enzyme is a type IIS that digests a double stranded DNA to produce a sticky end away from its recognition site and the first restriction enzyme is another type IIS that digests a double stranded DNA away from its recognition site and preferably produces a blunt end cut in the DNA. In even preferred embodiments, the second restriction enzyme is BsaI and the first restriction enzyme is MlyI.

In certain embodiments, a barcode is placed between the first restriction site and the target binding sequence and/or the target binding sequence and the second restriction site.

In certain embodiments, the probe construction can start directly from double stranded pre-downstream probes, therefore skipping the first PCR step to convert the single stranded to double stranded molecules or simply performing the PCR to amplify the amount of pre-upstream probes.

The sequence of the steps of digesting with the second restriction enzyme and the step of digesting with the first restriction enzyme can be interchanged or occur simultaneously. Particularly, digestion with the first restriction enzyme preferably producing blunt end can be performed first followed by the digestion with the second restriction enzyme producing overhangs and ligation with the second exonuclease protected adapter. In certain embodiments, the overhang can be at least 1, 2, 3, 4, 5 or more nucleotides. In preferred embodiments, the overhang is 1-5 nucleotides, more preferably 1-3 nucleotides, and most preferably 1-2 nucleotides. Regardless of the sequence of digestions, same double stranded ligation probe would be produced at the end of both digestions and ligation.

As shown in FIG. 4, the ligation probe is produced in a double stranded format. The upper strand having modifications on the 5' end corresponds to the extension probe discussed earlier in this disclosure. The other strand having the modifications on the 3' end corresponds to the ligation probe discussed earlier in this disclosure. Thus, in the double stranded downstream probe produced according to the methods disclosed herein, one strand is a ligation probe suitable for analyzing one of the strands of the target genomic region and the other strand is an extension probe suitable for analyzing the other strand of the target genomic region.

Figure 5:
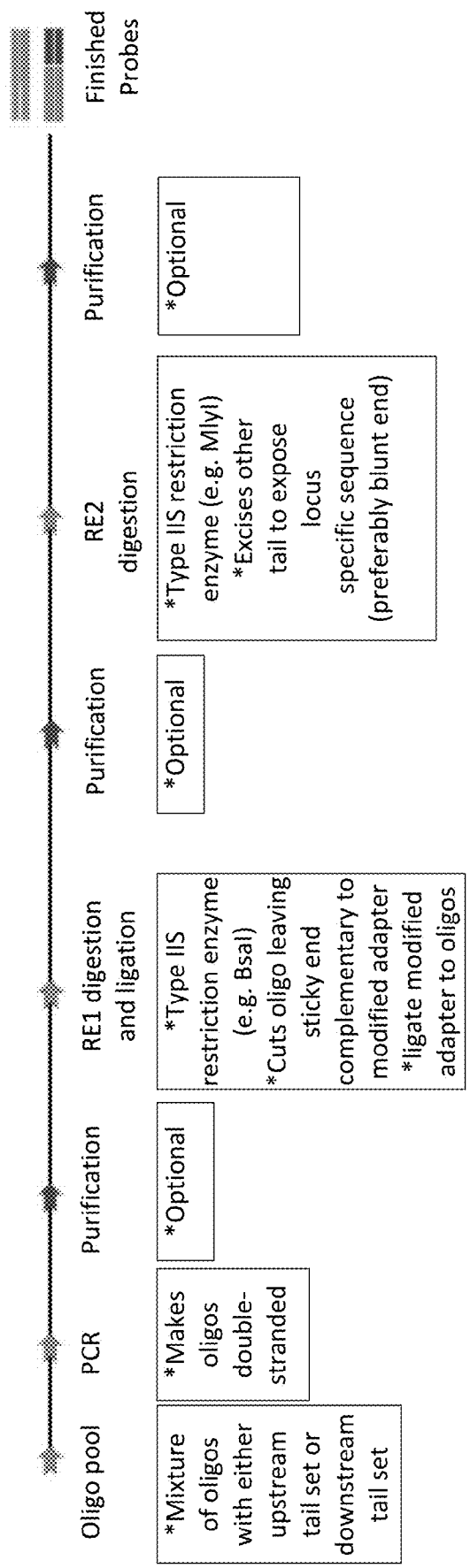
FIG. 5. Outline of the methods of producing upstream or downstream probes in double stranded form.

FIG. 5 describes the general scheme of producing the double stranded upstream and downstream probes. As a person of ordinary skill in the art will appreciate, in a double stranded upstream probe produced according to the methods discussed above, the strand comprising the modifications at the 5' end can be used as an extension probe and the strand comprising the modifications at the 3' end can be used as a ligation probe. Conversely, in a double stranded downstream probe produced according to the methods discussed above, the strand comprising the modifications at the 3' end can be used as a ligation probe and the strand comprising the exonuclease protection at the 5' end can be used as an extension probe. Accordingly, an embodiment of the invention provides a method of producing a double stranded oligonucleotide probe having a genetic modification on both strands at one end, the method comprising:

a) providing a single stranded or double stranded pre-probe comprising from the 5' end towards the 3' end: a first tail containing a first restriction site for a first restriction enzyme, a target binding sequence, a second tail containing a second restriction site for a second restriction enzyme, wherein the double stranded pre-probe is optionally produced in a PCR using appropriate primers to copy the single stranded pre-probe, b) optionally, performing a tail-swap reaction to substitute a temporary first or second tail for a permanent tail that is genetically modified to comprise at least a portion of a new desired sequence comprising:
  i) digesting the double stranded pre-probe with one of the restriction enzymes to remove one tail, or a portion of it, to produce an overhang, and
  ii) ligating to the double stranded probe digested the restriction enzyme to the permanent tail, the permanent tail molecule that contains genetic modifications and at least a portion of the permanent tail comprising an overhang that is complementary to the overhang of the digested double stranded probe, c) optionally, purifying the double stranded pre-probe ligated to the permanent tail, d) producing a double stranded probe by digesting the double stranded pre-probe with one tail or with the permanent tail ligated in place of the one tail with one restriction enzyme to remove either one tail or, in the situation in which one tail has been swapped, the other tail and produce a sticky end or, preferably, a blunt end within the target binding sequence, and e) optionally, purifying the double stranded probe. In some embodiments, the double stranded probes can be converted into single stranded probes by methods known in the art, for example denaturation of the double stranded probes or by selectively degrading one of the strands.

In preferred embodiments, one restriction enzyme is a type IIS that digests a double stranded DNA to produce a sticky end away from its recognition site and the other restriction enzyme is another type IIS that digests a double stranded DNA away from its recognition site and preferably produces a blunt end cut in the DNA. In even preferred embodiments, one of the restriction enzymes is BsaI and the other restriction enzyme is MlyI.

In certain embodiments, a barcode is placed between the first restriction site and the target binding sequence and/or the target binding sequence and the second restriction site.

In certain embodiments, the probe construction can start directly from double stranded pre-probes, therefore skipping the first PCR step to convert the single stranded to double stranded molecules.

The sequence of the steps of digesting with the second restriction enzyme and the step of digesting with the first restriction enzyme can be interchanged or occur simultaneously. Particularly, digestion with the restriction enzyme preferably producing blunt end can be performed first followed by the digestion with the restriction enzyme producing overhangs and ligation with the swapped adapter. In certain embodiments, the overhang can be at least 1, 2, 3, 4, 5 or more nucleotides. In preferred embodiments, the overhang is 1-5 nucleotides, more preferably 1-3 nucleotides, and most preferably 1-2 nucleotides. Regardless of the sequence of digestions, same double stranded ligation probe would be produced at the end of both digestions and ligation.

The double stranded probes can be used to capture and analyze both strands of a target genomic region of a double stranded genome. Therefore, certain embodiments of the invention provide a method of capturing a target genomic region from a double stranded target genetic material. The method comprises the steps of:

a) providing a pair of double stranded probe, where each strand of each double stranded probe corresponds to a ligation and extension probe, respectively,
wherein the double stranded probe upstream to the target comprises:
  i) a first extension probe comprising toward the 3' end a first target binding sequence and toward the 5' end a first primer binding sequence, and
  ii) a second ligation probe comprising toward the 5' end a first target binding sequence and toward the 3' end a first primer binding sequence,
and wherein the double stranded probe downstream to the target comprises:
  i) a first ligation probe comprising toward the 5' end a second target binding sequence and toward the 3' end a second primer binding sequence, and
  ii) a second extension probe comprising toward the 3' end a second target binding sequence and toward the 5' end a second primer binding sequence;
b) contacting the double stranded target genomic region with the double stranded extension probe and the double stranded ligation probe, the contacting performed under conditions to allow:
  i) denaturation of the double stranded upstream probe and the double stranded downstream probe into the first extension probe, the second ligation probe, the first ligation probe and the second extension probe, and
  ii) hybridization of the first extension probe and the first ligation probe to a first DNA strand in the target genomic region and hybridization of the second extension probe and the second ligation probe to a second DNA strand in the target genomic region,
c) amplifying the 3' end of the first extension probe until the 3' end of the amplified first extension probe is adjacent to the 5' end of the first ligation probe and amplifying the 3' end of the second extension probe until the 3' end of the amplified second extension probe is adjacent to the 5' end of the second ligation probe; and
d) capturing the target genomic region from the double stranded target genetic material by:
  i) ligating the 3' end of the amplified first extension probe with the 5' end of the first ligation probe to produce a first ligated probe, the first ligated probe comprising, from the 5' end to the 3' end, the first primer binding sequence, the first target binding sequence, the amplified target genomic region, the second target binding sequence, and the second primer binding sequence, and
  ii) ligating the 3' end of the amplified second extension probe with the 5' end of the second ligation probe to produce a second ligated probe, the second ligated probe comprising, from the 5' end to the 3' end, the second primer binding sequence, the second target binding sequence, the amplified target genomic region, the first target binding sequence, and the first primer binding sequence.

As a person of ordinary skill in the art will appreciate, in a pair of a double stranded upstream probe and a double stranded downstream probe the target binding sequences in the upstream probe and the downstream probe are designed so that they flank the target genomic region.

Also, the methods described above to synthesize the double stranded upstream and downstream probes can be used to produce the double stranded probes used in the methods disclosed herein for capturing both strands of a target genomic region. Therefore, in certain embodiments, the upstream probe comprises an exonuclease protection at the 5' end of the first extension probe and an exonuclease protection at the 3' end of the second ligation probe. Similarly, the downstream probe comprises an exonuclease protection at the 3' end of the first ligation probe and an exonuclease protection at the 5' end of the second extension probe.

The exonuclease protection at the ends of the extension and/or ligation probes can comprises one or more of: introducing thiophosphate linkages between nucleotides, incorporating two or more phosphoramidite and phosphoromonothioate and/or phosphorodithioate linkages, replacing one or more phosphodiester linkages between adjacent nucleotides by a formacetal/ketal linkage, blocking the 3' terminal hydroxyl group by a phosphoryl or acetyl group, introducing 3' terminal phosphoroamidate, introducing peptide nucleic acids (PNAs) or locked nucleic acids (LNAs), introducing one or more thiophosphate groups, or introducing a 2-O-methyl ribose sugar group in the oligonucleotide backbone.

After the first and the second ligated probes are produced, they can be isolated from the reaction mixture. Such isolating can comprises digesting the unwanted parts of the reaction mixtures, such as unincorporated probes or target genomic DNA, by treating the reaction mixture with one or more exonucleases having a 5'-3' exonuclease activity and a 3'-5' exonuclease activity. Because both the first and the second ligated probes have protections at both 5' and 3' ends, an exonuclease or a combination of exonucleases that provides both a 5'-3' exonuclease activity and a 3'-5' exonuclease activity can be used.

The target genomic region can be between about 10 bp and about 100 bp, between about 100 bp and about 300 bp, between about 300 bp and about 1,000 bp or between about 1,000 bp and about 20,000 bp.

Once isolated, the first and the second ligated probes can be amplified using specific primer pairs. Thus, further steps of analyzing the captured target genomic region comprise: amplifying the first and/or the second ligated probe in a polymerase chain reaction (PCR) using an amplification primer pair to produce copies of the first and/or the second ligated probe in a double stranded form, wherein the first ligated probe amplification primer pair comprising:

i) a first extension probe amplification primer comprising from 5' to the 3' end, one or more of: a first sequencing primer binding sequence, a first identifier sequence, and the first primer sequence, and ii) a first ligation probe amplification primer comprising from the 5' to the 3' end, one or more of: a second sequencing primer binding sequence, a second identifier sequence, and the second primer sequence; and wherein the second ligated probe amplification primer pair comprising:

i) a second extension probe amplification primer comprising from the 5' to the 3' end, one or more of: a third sequencing primer binding sequence, a third identifier sequence, and the second primer sequence, and ii) a second ligation probe amplification primer comprising from the 5' to the 3' end, one or more of: a fourth sequencing primer binding sequence, a fourth identifier sequence, and the first primer sequence.

A person skilled in the art can design appropriate sequences for the first and the second primer binding sequences and they can be same or different. Also, the first, second, third and fourth sequencing primers can have identical or different sequences. Preferably, the first, second, third and fourth identifier sequences have different sequences.

Once amplified, the double stranded ligated probes can be sequenced as discussed earlier in this disclosure in connection with the methods of capturing a single strand of the target genomic regions.

Similar to the design of the single stranded probes, the target sequences flank the target genomic region. Also, the sequence at the 3' ends of the first and the second extension probe hybridize to the corresponding target sequences on the genetic material and the sequences at the 5' end of the first and the second ligation probes hybridize to the corresponding target sequence on the genetic material. Thus, the extension probe and the ligation probe bind to the corresponding target sequences and these target sequences flank the target genomic region. Also, in certain embodiments, each of the extension and ligation probes hybridizes non-adjacently to that the first and the second target sequences flank the target genomic region. Also, the first and the second primer binding sequences on the double stranded extension and ligation probes can be same or different.

A person of ordinary skill in the art will appreciate that each of the double stranded probes used herein can be called "a double stranded upstream probe" or "a double stranded downstream probe" because one strand of each of the double stranded probes can be used as a ligation probe and the other strand can be used an extension probe. Therefore, the description used herein is based on the ease of reference calling one of the probes "a double stranded downstream probe" and the other probe "a double stranded upstream probe". An example of a combination of a "double stranded downstream probe" and a "double stranded upstream probe" is provided at the bottom of FIG. 4.

Similarly, the first target binding sequence present in the first extension probe is reverse complementary to the first target binding sequence present in the second ligation probe. Also, the second target binding sequence present in the first ligation probe is reverse complementary to the second target binding sequence present in the second extension probe. Therefore, the description used herein of the "first target binding sequence" and the "second target binding sequence" is for the ease of reference. This relationship between these sequences is apparent from the combination of the double stranded extension probe and the double stranded ligation probe provided at the bottom of FIG. 4. Therefore, when the first and the second ligated probes are produced, the two ligated probes contain reverse complementary copies of the target genomic region. As such, both strands of the target genomic region are captured.

Each of the double stranded upstream probe and the double stranded downstream probe can contain a minimum of between about 20 and about 200 nucleotides. Particularly, the first target binding sequence can be at least between about 10 and about 60 nucleotides. The first primer binding sequence can also be at least between about 10 and about 30 nucleotides. Similarly, the second target sequence can be at least between about 10 and about 60 nucleotides and the second primer binding sequence can be at least between about 10 and about 30 nucleotides. The specificity of the probes towards the target binding sites can be controlled by the lengths of the first and the second target binding sequences. Particularly, longer lengths of the first and the second target binding sequences provide higher binding specificity and shorter lengths of the first and the second target binding sequences provide lower specificity. A person of ordinary skill in the art can determine appropriate sequences for the first and the second target binding sequences based on the sequence of the target genomic region and the available genomic sequence for a particular organism, for example, from a genome sequence database.

The details of the hybridization, extension, ligation, removal of unwanted materials, amplification of the ligated probes, exonuclease protection of probes, incorporation of sample specific identifiers (also referenced in the art as indexes, barcodes, zip codes, adapters, etc.), and the sequencing of the target genomic regions discussed above with respect to single stranded extension and ligation probes. These details are also applicable to the methods of using the double stranded probes used herein.

In certain embodiments, multiple target genomic regions are captured and optionally, further analyzed, such as detected or sequenced. For a plurality of target genomic regions, a plurality of pairs of double stranded upstream and downstream probes is used. Each pair of double stranded upstream and downstream probes contains unique first and second target binding sequences, depending on the sequence flanking the target genomic region. However, each of the plurality of pairs of upstream and downstream probes can have the same first primer binding sequences and/or the same second primer binding sequences.

Accordingly, certain embodiments of the materials and methods disclosed herein provide for capturing a plurality of target genomic regions from a genetic material. The methods comprise the steps of:

a) hybridizing a plurality of pairs of double stranded probes to a plurality of pairs of target sequences, wherein each pair of the target sequences flanks one target genomic region from the plurality of target genomic regions, and wherein each pair of probes comprises a double stranded upstream probe and a double stranded downstream probe and for each pair of double stranded probes comprises:

a double stranded upstream probe comprising:

i) a first extension probe comprising toward the 3' end a first target binding sequence and toward the 5' end a first primer binding sequence, and ii) a second ligation probe comprising toward the 5' end a first target binding sequence and toward the 3' end a first primer binding sequence, and a double stranded downstream probe comprising:

i) a first ligation probe comprising toward the 3' end a second target binding sequence and toward the 5' end a second primer binding sequence, and ii) a second extension probe comprising toward the 3' end a second target binding sequence and toward the 5' end a second primer binding sequence;

wherein the first target binding sequence and the second target binding sequence bind respectively to a first target sequence and a second target sequence that flank a target genomic region;

b) amplifying the 3' ends of the first extension probes until the 3' ends of the amplified first extension probes are adjacent to the 5' ends of the first ligation probes and amplifying the 3' ends of the second extension probes until the 3' ends of the amplified second extension probes are adjacent to the 5' ends of the second ligation probes; and c) capturing the plurality of target genomic regions from the double stranded target genetic material by:

i) ligating the 3' ends of the amplified first extension probes with the 5' ends of the first ligation probes to produce a plurality of first ligated probes, each of the first ligated probes comprising, from the 5' ends to the 3' ends, the first primer binding sequence, the first target binding sequence, the amplified target genomic region, the second target binding sequence, and the second primer binding sequence, and ii) ligating the 3' ends of the amplified second extension probes with the 5' ends of the second ligation probes to produce a plurality of second ligated probe, each second ligated probe comprising, from the 5' ends to the 3' ends, the second primer binding sequence, the second target binding sequence, the amplified target genomic region, the first target binding sequence, and the first primer binding sequence.

The aspects described above of capturing a target genomic region, for example, designing the double stranded upstream and downstream probes, the lengths of the target genomic regions, the first and second primer binding sequences are also applicable to the instant methods of capturing a plurality of target genomic regions using a plurality of double stranded upstream and downstream probes.

In certain embodiments, each of the plurality of captured target genomic regions can be sequenced in methods comprising amplification and sequencing of the ligated probes. Details provided above with respect to these steps are also applicable to the methods of capturing and analyzing a plurality of double stranded target genomic regions.

Further embodiments of the invention also provide kits comprising one or more pairs of double stranded probes. Each pair of double stranded probe comprises a double stranded upstream probe and a double stranded downstream probe, wherein wherein the double stranded upstream probe comprises:

i) a first extension probe comprising toward the 3' end a first target binding sequence and toward the 5' end a first primer binding sequence, and ii) a second ligation probe comprising toward the 5' end a first target binding sequence and toward the 3' end a first primer binding sequence, and wherein the double stranded downstream probe comprises:

i) a first ligation probe comprising toward the 5' end a second target binding sequence and toward the 3' end a second primer binding sequence, and ii) a second extension probe comprising toward the 3' end a second target binding sequence and toward the 5' end a second primer binding sequence.

The double stranded upstream probe can comprise an exonuclease protection at the 5' end of the first extension probe and an exonuclease protection at the 3' end of the second ligation probe and the double stranded downstream probe can comprise an exonuclease protection at the 3' end of the first ligation probe and an exonuclease protection at the 5' end of the second extension probe. The exonuclease protection can comprise one or more of: thiophosphate linkages between nucleotides, two or more phosphoramidite and phosphoromonothioate and/or phosphorodithioate linkages, one or more phosphodiester linkages between adjacent nucleotides by a formacetal/ketal linkage, blocked 3' terminal hydroxyl group by a phosphoryl or acetyl group, 3' terminal phosphoroamidate, peptide nucleic acids (PNAs) or locked nucleic acids (LNAs), one or more thiophosphate groups, or a 2-O-methyl ribose sugar group in the oligonucleotide backbone.

The following example illustrates an embodiment of the procedures for practicing the invention. This example should not be construed as limiting.

Example 1—Preparing a Pair of Double Stranded Upstream and Downstream Probes

Figure 6:
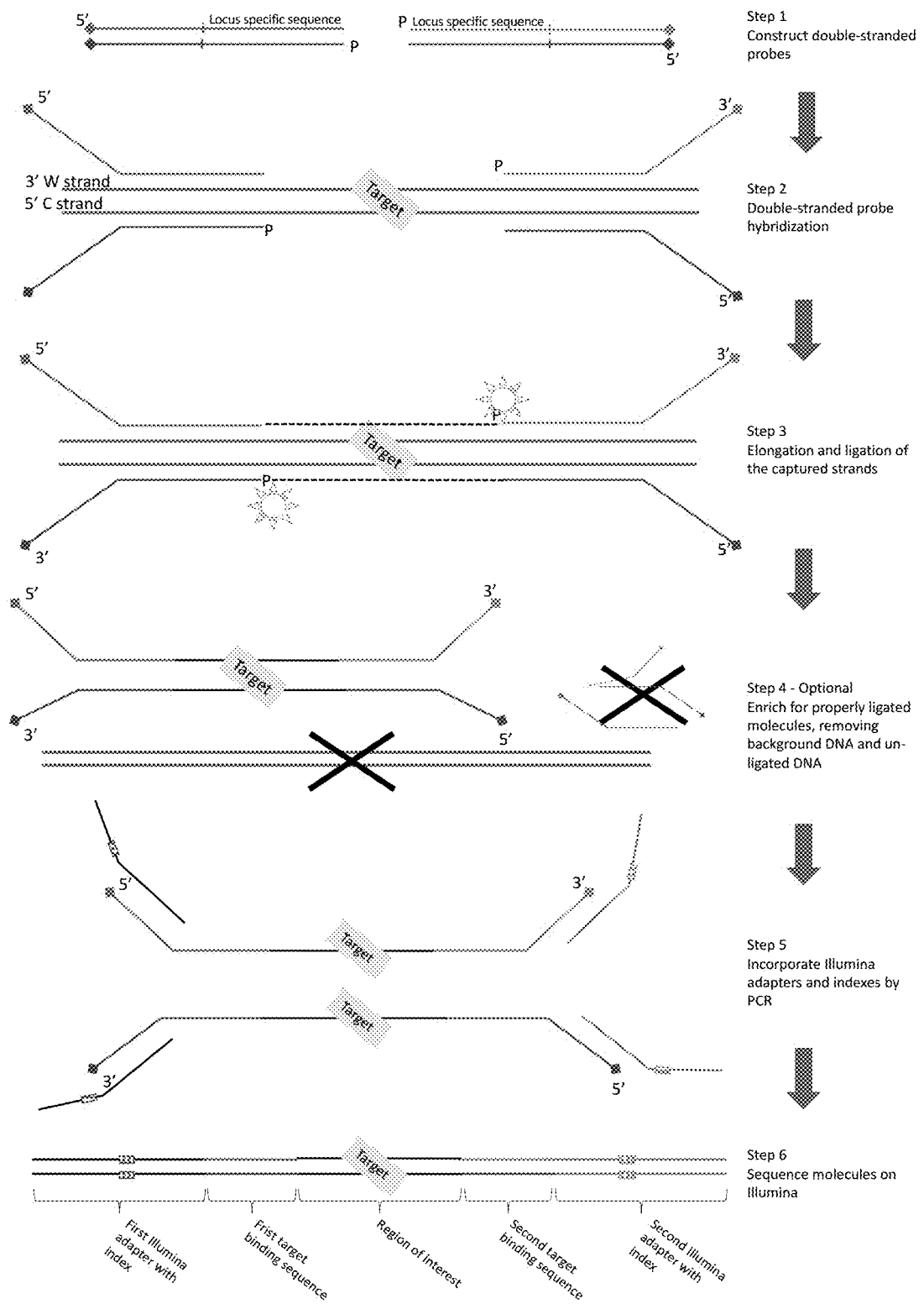
FIG. 6. Overview of one example of a method of using double stranded upstream and downstream probes for analyzing both strands of a target genomic region. The double stranded upstream and downstream probes, (for example, as prepared via methods exemplified in FIG. 3 or 4, respectively) can be used for analyzing both strands of a target genomic region.

Two sets of double-stranded probes that will hybridize to both strands of the DNA around the target regions are produced. FIG. 6 illustrates the overview of the reaction utilizing double-stranded probes that hybridize to both strands of a target genomic region.

For a target genomic region, a pair of probes is designed so that it hybridizes downstream and upstream of the target region. The upstream probe is referenced herein as left probe or i5 probe, whereas the downstream probe is referenced herein as the right probe or i7 probe. The regions of probes that hybridize to the target are called Loci Specific Sequence (LSS) and can be designed based on the sequences that flank the target genomic region based on sequence complementarity. To form the single stranded pre-extension and pre-ligation probes, four universal tails are appended to the LSS to their respective 3' and 5' ends. The four tails are different from each other but are the same across all targets. Therefore, the sequences of the pre-probes are as follows:

pre-upstream probe: 5' Tail 1-LSS1-Tail 2:
pre-downstream probe: 5' Tail 3-LSS2-Tail 4:

Where LSS1 and LSS2 have at least 10 bases, preferably, between 10 and 60 bases.

The tails contain recognition sequences for restriction enzymes on either side and a binding region for the PCR primers. The probe construction begins by synthesizing the pre-probe oligonucleotides in single stranded form. These can be synthesized individually and pooled through conventional approaches or be synthesized in parallel. Once the pool of pre-probes is synthesized and in solution, the first step of PCR is conducted to produce the double stranded pre-probes. The PCR is conducted using the appropriate primers, in two independent reactions, one primer pair amplifying the downstream pre-probes and another primer pair amplifying the upstream pre-probes:

| Primer name | Sequence |
|---|---|
| preprobe_PCR_up_1 | Hybridizes to tail 2 |
| preprobe_PCR_up_2 | Hybridizes to the complement of tail 1 |
| preprobe_PCR_down_1 | Hybridizes to tail 4 |
| preprobe_PCR_down_2 | Hybridizes to the complement of tail 3 |

The products of the upstream PCR are processed to remove tail 2 by digestion with an enzyme preferably producing a blunt end and swap tail 1 with an adapter containing modified oligonucleotides through a combination of enzymatic reactions. Similarly, the products of the downstream PCR are processed to remove the tail 3 by digestion with an enzyme preferably producing a blunt end and swap the tail 4 with another adapter containing modified oligonucleotides.

As shown in FIG. 6, these probes are double-stranded and fully complementary to each other and, therefore, tend to hybridize and remain in double stranded form. However, under the appropriate reaction conditions, for example, a denaturation step, the double stranded probes are converted into single stranded form and hybridize to the corresponding sequences on the target genomic region. The double stranded probes can be converted into single stranded probes by various means known in the art, for example, denaturation or by selectively degrading one of the strands. Using the double stranded probes allows capturing both strands of the target genomic regions and, as compared to reactions with single-stranded probes, increased efficiency, uniformity and yield is achieved. Increased efficiency is achieved, in part, because the chance of capturing the target region are doubled as the probes capturing each strand may have different optimal hybridization conditions, and in case one of the pairs of ligation and extension probes fails to hybridize, the other pair might still bind and capture the target. Increased uniformity is achieved, in part, because certain conditions for base composition and hybridization kinetics between the two strands are optimal within different variations across different target genomic loci. Finally, the yield is increased, in part, because, as compared to reactions using single-stranded probes, the amount of captured target genomic regions is doubled.

All patents, patent applications, provisional applications, and publications referred to or cited herein are incorporated by reference in their entirety, including all figures and tables, to the extent they are not inconsistent with the explicit teachings of this specification.

It should be understood that the embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

1. Campbell, N. R., Harmon, S. A., and Narum, S. R. (2015). Genotyping-in-Thousands by sequencing (GT-seq): A cost effective SNP genotyping method based on custom amplicon sequencing. *Mol. Ecol. Resour.* 15, 855-867. doi: 10.1111/1755-0998.12357.

2. Gnirke, A., Melnikov, A., Maguire, J., Rogov, P., LeProust, E. M., Brockman, W., et al. (2009). Solution hybrid selection with ultra-long oligonucleotides for massively parallel targeted sequencing. *Nat Biotechnol* 27, 182-189. doi:nbt.1523 [pii]10.1038/nbt.1523.

3. Shen, P., Wang, W., Krishnakumar, S., Palm, C., Chi, A.-K., Enns, G. M., et al. (2011). High-quality DNA sequence capture of 524 disease candidate genes. *Proc. Natl. Acad. Sci. U.S.A.* 108, 6549-54. doi:10.1073/pnas.1018981108.

4. U.S. Pat. No. 8,808,991.

5. U.S. Pat. No. 8,460,866.

6. PCT Publication WO 2005/118847.

7. PCT Publication WO 2009/079488.

8. Krishnakumar, S., Zheng, J., Wilhelmy, J., Faham, M., Mindrinos, M., and Davis, R., *PNAS* (2008) 105(27): 9296-9301.

9. U.S. Pat. No. 8,795,968.

10. U.S. Patent Application Publication Number 2008/0026393.

11. El-Sagheer et al. (2011), *PNAS;* 108 (28) 11338-11343.

12. U.S. Pat. No. 4,656,127.

13. Shaw et al., 1991, *Nucleic Acids Research,* 19, 747-750.

14. Raney et al., 1998, *Peptide Nucleic Acids* (Nielsen, P. E., and Egholm, M., Eds.) Horizon Scientific Press, Wymondham, U.K.

15. Simeonov et al., *Nucl. Acids Res.* 2002, Vol. 30, e31.

16. Jacobsen et al., *Int. Biot. Lab, February* 2001, 18.

We claim:

1. A method of producing a double stranded oligonucleotide probe optionally having modifications on both strands at one end, the method comprising:

a) providing a single stranded or double stranded pre-probe comprising from the 5' end towards the 3' end: a first tail, a first restriction site for a first restriction enzyme, a target binding sequence, a second restriction site for a second restriction enzyme, and a second tail, wherein the double stranded pre-probe is optionally produced in a PCR using appropriate primers to copy the single stranded pre-probe, b) optionally, performing a tail-swap reaction to substitute a temporary first or second tail for a permanent tail that is genetically modified to comprise at least a portion of a new desired sequence comprising:

i) digesting the double stranded pre-probe with the first restriction enzyme to remove the first pre-tail, or a portion of it, to produce an overhang, and ii) ligating the double stranded pre-probe digested with the first restriction enzyme to the permanent tail, the permanent tail molecule that contains genetic modifications and at least a portion of the permanent tail comprising an overhang that is complementary to the overhang of the digested double stranded pre-probe, c) optionally, purifying the digested double stranded pre-probe ligated to the permanent tail, d) producing a double stranded probe by digesting the double stranded pre-probe with the second restriction enzyme to remove the second tail and produce a blunt end or sticky end within the target binding sequence, wherein the double stranded probe hybridizes to:

i) a sense nucleotide sequence upstream of a target nucleotide sequence and to an antisense nucleotide sequence upstream of the target nucleotide sequence, or ii) a sense nucleotide sequence downstream of the target nucleotide sequence and to an antisense nucleotide sequence downstream of the target nucleotide sequence, e) optionally, purifying the double stranded probe, and f) producing a double stranded upstream probe and a double stranded downstream probe according to steps a) through e), wherein the double stranded upstream probe hybridizes to the sense nucleotide sequence upstream of the target nucleotide sequence and to the antisense nucleotide sequence upstream of the target nucleotide sequence; and the double stranded downstream probe hybridizes to the sense nucleotide sequence downstream of the target nucleotide sequence and to the antisense nucleotide sequence downstream of the target nucleotide sequence.

2. The method of claim 1, wherein the single stranded pre-probe comprises a barcode between the first restriction site and the target binding sequence and/or the target binding sequence and the second restriction site.

3. The method of claim 1, wherein the first and the second restriction enzymes are Type IIS restriction enzymes that cleave a double stranded DNA away from its recognition site.

4. The method of claim 1, wherein the genetic modifications of the permanent tail confer exonuclease protection, incorporate detectable nucleotides or modified nucleotides.

5. The method of claim 1, wherein the pre-probe or double stranded probe comprises between about 20 and about 200 nucleotides.

6. The method of claim 5, wherein the first tail is between 10 to 30 nucleotides, the target binding sequence is between 10 and 60 nucleotides, and the second tail is between 10 to 30 nucleotides.

7. The method of claim 1, said method further comprising converting the double stranded probes to single stranded probes.

8. A method of producing a double stranded oligonucleotide probe optionally having modifications on both strands at one end, the method comprising:

a) providing a single stranded or double stranded pre-probe comprising from the 5' end towards the 3' end: a first tail, a first restriction site for a first restriction enzyme, a target binding sequence, a second restriction site for a second restriction enzyme, and a second tail, wherein the double stranded pre-probe is optionally produced in a PCR using appropriate primers to copy the single stranded pre-probe, b) performing a tail-swap reaction to substitute a temporary first or second tail for a permanent tail that is genetically modified to comprise at least a portion of a new desired sequence comprising:

i) digesting the double stranded pre-probe with the first restriction enzyme to remove the first pre-tail, or a portion of it, to produce an overhang, and ii) ligating the double stranded pre-probe digested with the first restriction enzyme to the permanent tail, the permanent tail molecule that contains genetic modifications and at least a portion of the permanent tail comprising an overhang that is complementary to the overhang of the digested double stranded pre-probe, c) purifying the digested double stranded pre-probe ligated to the permanent tail, d) producing a double stranded probe by digesting the double stranded pre-probe with the second restriction enzyme to remove the second tail and produce a blunt end or sticky end within the target binding sequence, wherein the double stranded probe hybridizes to:

i) a sense nucleotide sequence upstream of a target nucleotide sequence and to an antisense nucleotide sequence upstream of the target nucleotide sequence, or ii) a sense nucleotide sequence downstream of a target nucleotide sequence and to an antisense nucleotide sequence downstream of the target nucleotide sequence, e) purifying the double stranded probe, and f) producing a double stranded upstream probe and a double stranded downstream probe according to steps a) through e), wherein the double stranded upstream probe hybridizes to the antisense nucleotide sequence upstream of the target nucleotide sequence and to the sense nucleotide sequence upstream of the target nucleotide sequence; and the double stranded downstream probe hybridizes to the antisense nucleotide sequence downstream of the target nucleotide sequence and to the sense nucleotide sequence downstream of the target nucleotide sequence.

* * * * *